(12) United States Patent
Pearlman

(10) Patent No.: US 9,006,210 B2
(45) Date of Patent: Apr. 14, 2015

(54) COMPOSITIONS AND METHODS FOR TREATING CORNEAL INFLAMMATION

(75) Inventor: Eric Pearlman, Lakeline, OH (US)

(73) Assignee: Case Western Reserve University, Cleveland, OH (US)

(*) Notice: Subject to any disclaimer, the term of this patent is extended or adjusted under 35 U.S.C. 154(b) by 105 days.

(21) Appl. No.: 12/997,444

(22) PCT Filed: Jun. 15, 2009

(86) PCT No.: PCT/US2009/047407
§ 371 (c)(1),
(2), (4) Date: Dec. 10, 2010

(87) PCT Pub. No.: WO2009/152517
PCT Pub. Date: Dec. 17, 2009

(65) Prior Publication Data
US 2011/0105426 A1    May 5, 2011

Related U.S. Application Data

(60) Provisional application No. 61/101,493, filed on Sep. 30, 2008, provisional application No. 61/061,291, filed on Jun. 13, 2008.

(51) Int. Cl.
*A61K 31/7016* (2006.01)
*A61P 27/02* (2006.01)
*A61P 29/00* (2006.01)
*A61P 31/04* (2006.01)
*A61K 31/665* (2006.01)

(52) U.S. Cl.
CPC .................................. *A61K 31/665* (2013.01)

(58) Field of Classification Search
CPC combination set(s) only.
See application file for complete search history.

(56) References Cited

U.S. PATENT DOCUMENTS

| 6,719,929 | B2 | 4/2004 | Winterton et al. |
| 2001/0045676 | A1 | 11/2001 | Winterton et al. |
| 2004/0266702 | A1* | 12/2004 | Dawson et al. ................. 514/28 |
| 2006/0051821 | A1 | 3/2006 | Rossignol et al. |
| 2008/0008749 | A1 | 1/2008 | Pearlman et al. |

FOREIGN PATENT DOCUMENTS

| CN | 101262870 A | 9/2008 |
| EP | 1939209 A1 | 2/2008 |
| JP | 2003509369 A | 3/2003 |
| WO | 0119367 A1 | 3/2001 |
| WO | 2007026675 A1 | 3/2007 |
| WO | 2007031879 A2 | 3/2007 |
| WO | WO 2008/076804 A2 | 6/2008 |

OTHER PUBLICATIONS

Khatri et al. Investigative Ophthalmology & Visual Science, Jul. 2002, vol. 43, No. 7, pp. 2278-2284.*
Johnson, Angela, C. et al., "Activation of Toll-Like Receptor (TLR)2, TLR4, and TLR9 in the Mammalian Cornea Induces MyD88-Dependent Corneal Inflammation", (*Invest Ophthalmol Vis Sci.* 2005;46:589-595).
Sun, Yan, et al., "*Staphylococcus aureus*-Induced Corneal Inflammation Is Dependent on Toll-Like Receptor 2 and Myeloid Differentiation Factor 88", Infection and Immunity, Sep. 2006, p. 5325-5332.
European Search Report dated Aug. 27, 2012.
Hutchinson, M.R., et al., "Evidence That Tricyclic Small Molecules May Possess Toll-Like Receptor and Myeloid Differentiation Protein 2 Activity", Neuroscience 168 (2010) 551-563.
Chinese Office Action dated Sep. 6, 2013.
Peri, Francesco, et al., "Therapeutic targeting of innate immunity with Toll-like receptor 4 (TLR4) antagonists", Biotechnology Advances 30 (2012) 251-260.
Hawkins, Lynn D., et al., "Inhibition of Endotoxin Response by Synthetic TLR4 Agonists", Current Topics in Medicine Chemistry, 2004, 4, 1147-1171.
Ianaro, A., et al., "New Insight in LPS Antagonist", Min-Reviews in Medical Chemistry, 2009, 9, 306-317.
Leon, Carlos G., et al., "Discovery and Development of Toll-Like Receptor 4 (TLR4) Antagonists: A New Paradigm for Treating for Treating Sepsis and Other Diseases", Pharmaceutical Research. vol. 25, No. 8, Aug. 2008, pp. 1751-1761.

* cited by examiner

*Primary Examiner* — Layla Bland
(74) *Attorney, Agent, or Firm* — Tarolli, Sundheim, Covell & Tummino LLP

(57) ABSTRACT

A method of treating corneal inflammation in a subject includes administering to the subject a therapeutically effective amount of a TLR4 antagonist.

26 Claims, 15 Drawing Sheets

COMPOSITIONS AND METHODS FOR TREATING CORNEAL INFLAMMATION

RELATED APPLICATION

This application corresponds to PCT/US09/47407, filed Jun. 15, 2009, which claims the benefit of U.S. Provisional Application No. 61/101,493, filed Sep. 30, 2008 and 61/061,291, filed Jun. 13, 2008, the subject matter, of which is incorporated herein by reference in its entirety.

TECHNICAL FIELD

The present invention relates to compositions and methods that are useful in the treatment and prevention of corneal inflammation and/or conditions related to corneal inflammation.

BACKGROUND OF THE INVENTION

Following an insult to the cornea, the immune and inflammatory systems respond to protect the integrity of the eye. This protective mechanism can have clinical manifestations ranging from cellular infiltration to ulcer formation. Though protective, these processes often compromise the primary function of the eye by causing vascularization, scarring and/or perforation of the cornea.

For example, it has been demonstrated that exposure of the abraded corneal surface to lipopolysaccharide (LPS) or other bacterial products induces corneal inflammation causing neutrophil-rich infiltrates in the corneal stroma (Johnson et al., *Invest. Ophthalmol Vis. Sci.* 2005; 46:589-595; Khatri et al., *Invest. Opthalmol. Vis. Sci.* 2002; 43:2278-2284; Schultz et al., *Infection and Immunity* 2000; 68:1731-1734; Schultz et al., *Exper. Eye Res.* 1997; 64:3-9; Sun et al., *Infection and Immunity* 2006; 74:5325-5332).

When there is an insult to the corneal surface, inflammatory and/or immune cells are sent to repair the damage. These cells can aggregate in a region of the cornea and are visible as clinically identifiable infiltrates. This infiltrate formation and resultant corneal inflammation can arise from either infectious or non-infectious conditions. One infectious condition that can adversely affect the cornea is bacterial keratitis. Major causes of bacterial keratitis in the USA and worldwide include infection by *Pseudomonas aeruginosa, Staphylococcus aureus, S. epidermidis* and *Streptococcus* species. In developing countries, bacterial keratitis is primarily associated with trauma related to agricultural work; whereas, in industrialized countries, bacterial keratitis is associated with contact lens wear.

In addition to infectious keratitis, contact lens wear is also associated with sterile, culture-negative clinical manifestations, including contact lens associated red eye (CLARE), contact lens peripheral ulcers (CLPU), and contact lens associated corneal infiltrates CLACI (Stapleton et al., *Optom Vis Sci.* 2007; 84:257-272). Although symptoms from these manifestations are less severe than symptoms associated with infectious keratitis, affected individuals have pain, redness, blurred vision and severe discomfort. Given that the number of contact lens wearers exceeds 34 million in the USA and 140 million worldwide, the relatively small percentage of contact lens wearers with these clinical manifestations translates to large total number of individuals affected (Stapleton et al., *Optom. Vis. Sci.* 2007; 84:257-272).

Currently, steroid use is the only treatment for corneal infiltrates. The side effects of steroid use are considerable. In infectious keratitis, steroids are given only after resolution of infection; otherwise, they can have an adverse effect on the infection. Furthermore, steroid use can cause increased ocular pressure, thereby increasing the risk of glaucoma, and are often administered together with anti-glaucoma treatment.

SUMMARY OF THE INVENTION

The present invention relates to a method of treating corneal inflammation in a subject. The method includes administering to the subject a therapeutically effective amount of a toll like receptor 4 (TLR4) antagonist to treat the corneal inflammation in the subject.

The present invention also relates to a method of treating corneal inflammation in a subject associated with contact lens wear. The method includes administering to the subject a therapeutically effective amount of a TLR4 antagonist to treat the corneal inflammation associated with contact lens wear.

The present invention also relates to a method of treating a TLR-induced inflammatory response in a subject's cornea. The method includes administering to the subject a therapeutically effective amount of a TLR4 antagonist to treat the TLR-induced inflammatory response.

The present invention also relates to a contact lens for treating corneal inflammation in a subject. The contact lens includes a substrate and a coating. The coating includes an amount of TLR4 antagonist effective in treating corneal inflammation in the subject.

The present invention further relates to an ophthalmic preparation for treating corneal inflammation in a subject. The ophthalmic preparation includes an ophthalmic solution and an amount of TLR4 antagonist effective in treating corneal inflammation in the subject.

The present invention also relates to a method of treating infectious keratitis in a subject. The method includes administering to the subject a therapeutically effective amount of a TLR4 antagonist and at least one of an antibacterial agent, antiviral agent, or antifungal agent.

DETAILED DESCRIPTION

Figure 1:
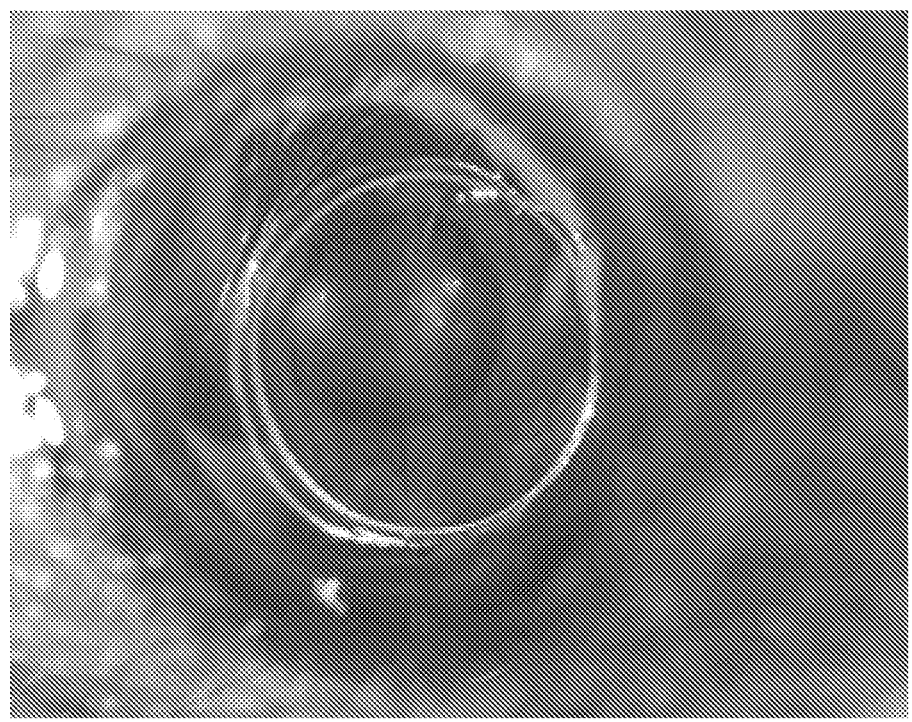
FIG. 1 illustrates a photograph of a contact lens applied to a surface of a cornea treated with eritoran tetrasodium in accordance with an aspect of a therapeutic method of the present invention.

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the term "Toll like receptor 4 antagonist" or "TLR4 antagonist" refers to an agent, such as a small molecule, polypeptide, polynucleotide, that is capable of substantially reducing, inhibiting, blocking, and/or mitigating the activation of TLR4 of a cell.

As used herein, the term "subject" refers to any warm-blooded organism including, but not limited to, human beings, pigs, rats, mice, dogs, goats, sheep, horses, monkeys, apes, rabbits, cattle, etc.

As used herein, the terms "treatment," "treating," or "treat" refers to any specific method or procedure used for the cure of, inhibition of, reduction of, elimination of, or the amelioration of a disease or pathological condition (e.g. corneal inflammation) including, for example, preventing corneal inflammation from developing, inhibiting corneal inflammation development, arresting development of clinical symptoms associated with corneal inflammation, and/or relieving the symptoms associated with corneal inflammation.

As used herein, the term "effective amount" refers to a dosage of a TLR4 antagonist administered alone or in conjunction with any additional therapeutic agents that are effective and/or sufficient to provide treatment of corneal inflammation and/or a disease or disorder associated with corneal inflammation. The effective amount can vary depending on the subject, the disease being treated, and the treatment being effected.

As used herein, the term "therapeutically effective amount" refers to that amount of a TLR4 antagonist administered alone and/or in combination with additional therapeutic agents that results in amelioration of symptoms associated with corneal inflammation and/or a disease or disorder associated with corneal inflammation and/or results in therapeutically relevant effect. By way of example, a "therapeutically effective amount" may be understood as an amount of TLR4 antagonist required to reduce corneal inflammation in a subject.

As used herein, the terms "parenteral administration" and "administered parenterally" refers to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

As used herein, "Unit dosage" formulations are those containing a dose or sub-dose of the administered ingredient adapted for a particular timed delivery. For example, "unit dosage" formulations are those containing a daily dose or unit or daily sub-dose or a weekly dose or unit or weekly sub-dose and the like.

As used herein the term "alkyl" refers to aliphatic organic groups which may be branched or straight and which may optionally be substituted with one or more halogen atoms at any position along the alkyl chain.

As used herein, the term "pharmaceutically acceptable salt" includes salts of compounds derived from the combination of the compound and an organic or inorganic acid or base.

The present invention relates generally to methods of treating corneal inflammation in a subject as well as to methods of mitigating corneal opacities (e.g., corneal haze, stromal haze, stromal thickness) associated with corneal inflammation. In one example, the corneal inflammation can be caused by and/or related to contact lens wear. In other examples, the corneal inflammation can be associated with uveitis, scleritis, episcleritis, keratitis, ocular or ophthalmic surgery (e.g., cornea surgery), endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, and pterygium.

According to an embodiment of a method of the present invention, corneal inflammation in a subject can be substantially reduced and/or mitigated by administering a TLR4 antagonist to the subject's cornea at an amount effective to block, inhibit, and/or mitigate activation of TLR4. One aspect of the present invention therefore relates to a method of treating corneal inflammation by administering to a subject a therapeutically effective amount of at least TLR4 antagonist to reduce and/or mitigate corneal inflammation in the subject.

In one embodiment of the present invention, the TLR4 antagonist used to treat corneal inflammation in the subject is a compound of formula (I):

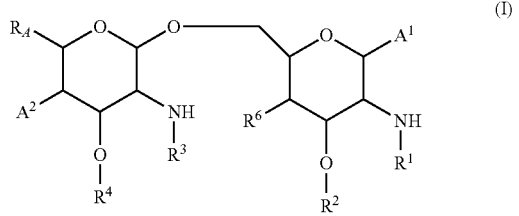
(I)

where $R^1$ is selected from the group consisting of:

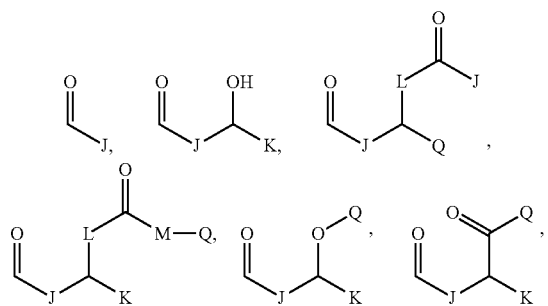

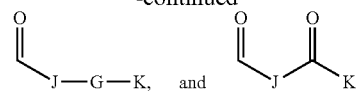

where each J, K, and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 alkyl,

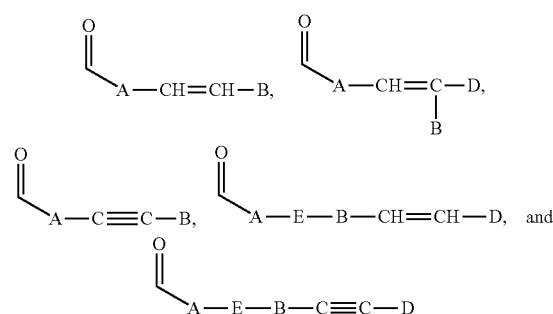

where E is NH, O, S, SO, or $SO_2$; each A, B, and D, independently, is straight or branched C1 to C15 alkyl;

$R^4$ is selected from the group consisting of straight or branched C4 to C20 alkyl, and

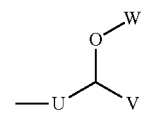

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J', -J'-OH, -J'-O—K', -J'-O—K'—OH, and -J'-O—$PO(OH)_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of OH,

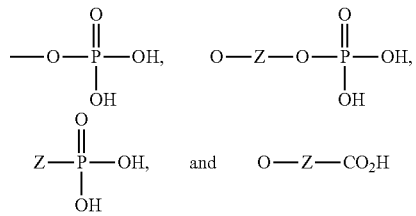

where Z is straight or branched C1 to C10 alkyl;

or pharmaceutically acceptable salt or phosphate ester thereof.

In one embodiment, the TLR4 antagonist of formula (I) is a compound of formula (II):

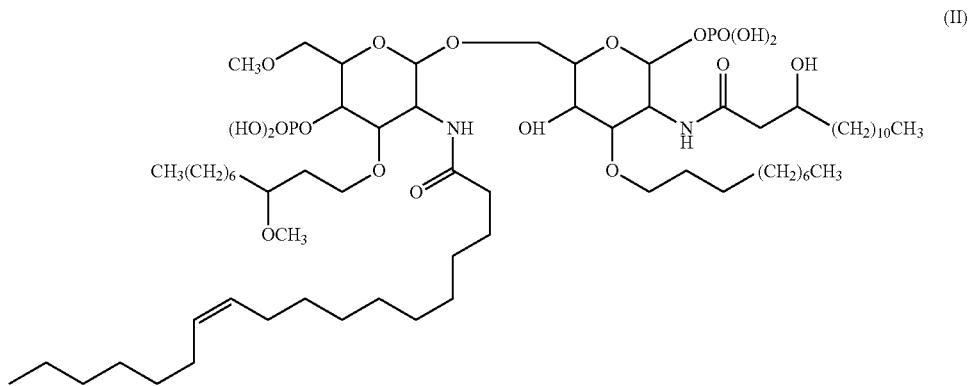

or a pharmaceutically acceptable salt or phosphate ester thereof.

In another embodiment, the TLR4 antagonist of formula (II) is:

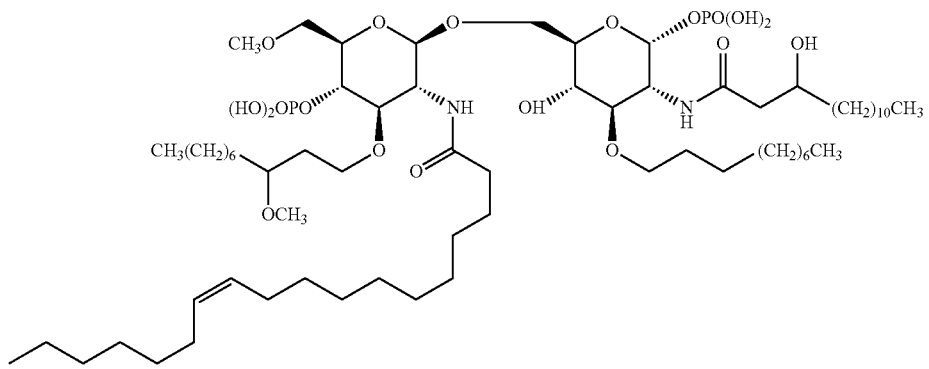

or a pharmaceutically acceptable salt or phosphate ester thereof.

In another embodiment, the TLR4 antagonist is eritoran tetrasodium (also known as compound E5664). Eritoran tetrasodium is the tetrasodium salt of the compound shown immediately above. Eritoran tetrasodium is described in U.S. Pat. No. 5,935,938.

Other TLR4 antagonists, which can be used to treat a subject with corneal inflammation in methods of the present invention include the following compounds:

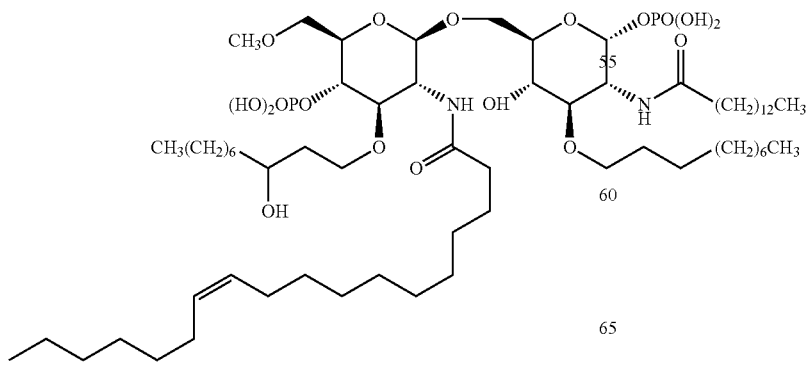

-continued
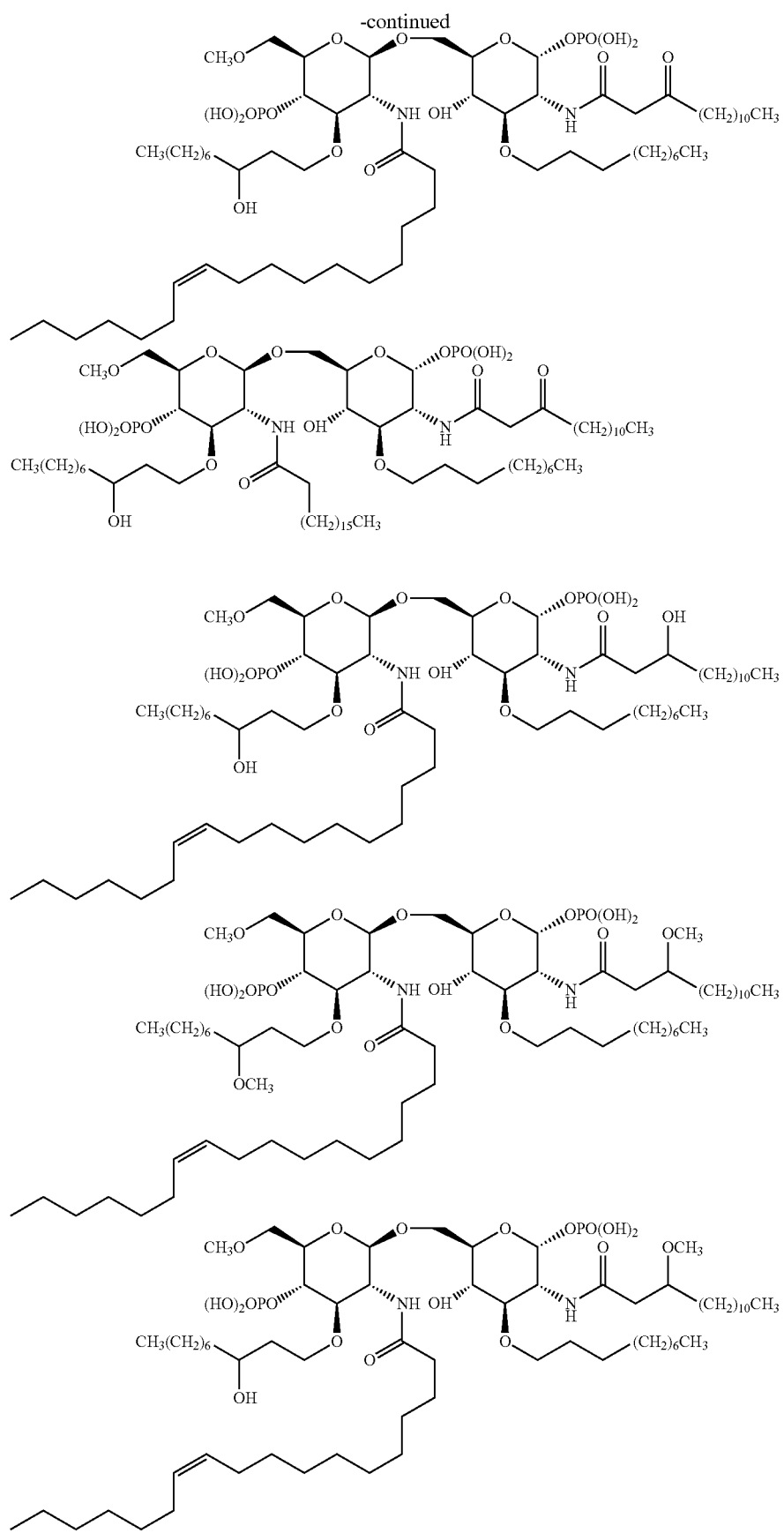

or pharmaceutically acceptable salts thereof or phosphate ester thereof (see U.S. Pat. App. No. 2007/0072824A1).

Additional TLR4 antagonists that can be used in the invention include, for example, compound B531 (U.S. Pat. No. 5,530,113), as well as other compounds described in the following patents: U.S. Pat. No. 5,935,389 (e.g., substituted liposaccharides identified by formula I); U.S. Pat. No. 5,612,476 (e.g., lipid A analogs disclosed at columns 2-41); U.S. Pat. No. 5,756,718 (lipid A analogs disclosed at columns 2-40); U.S. Pat. No. 5,843,918 (e.g., lipid A analogs disclosed at columns 2-48); U.S. Pat. No. 5,750,664 (e.g., substituted liposaccharides identified by formula I); U.S. Pat. No. 6,235,724 (e.g., lipid A analogs identified by formulas I and II); U.S. Pat. No. 6,184,366 (e.g., lipid A analogs identified by formula I), U.S. Pat. No. 5,681,824, U.S. Pat. App. Pub. No. 20030144503A1, and U.S. Pat. App. Pub. No. 20020028927A1. Methods for making these compounds are also described within these documents. Additional methods for making such compounds are described, for example, in WO 02/94019.

Still other examples of the TLR4 antagonists, which can be used to treat a subject with corneal inflammation according to methods of the present invention include compounds of formula (III):

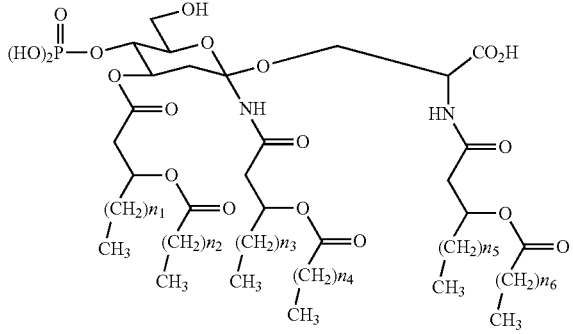

(III)

or a pharmaceutically acceptable salt or phosphate ester thereof; wherein $n_1$, $n_3$, and $n_5$, are the same or different and are positive integers from, for example, 1 to about 10 (e.g., 10); $n_2$, $n_4$, and $n_6$, are the same or different and are positive integers less than 8. Compounds of formula (III) are synthetic lipid A mimetics that do not stimulate cytokine production or other gene expression in human peripheral blood monocytes in vitro or induce an inflammatory response in vivo. (Stover et al. (*Journal of Biological Chemistry* Vol. 27, No. 6)).

In one example, at least one of $n_2$, $n_4$, and $n_6$ is less than 7 so that at least one secondary acyl group of formula (III) is less than 10 carbons. Compounds of formula (III) with at least one secondary acyl group less than 10 carbons have been shown to be potent TLR4 antagonists. (Stover et al. (*Journal of Biological Chemistry* Vol. 27, No. 6)).

In one embodiment, the TLR4 antagonist of formula (III) used in the present method has the following structure:

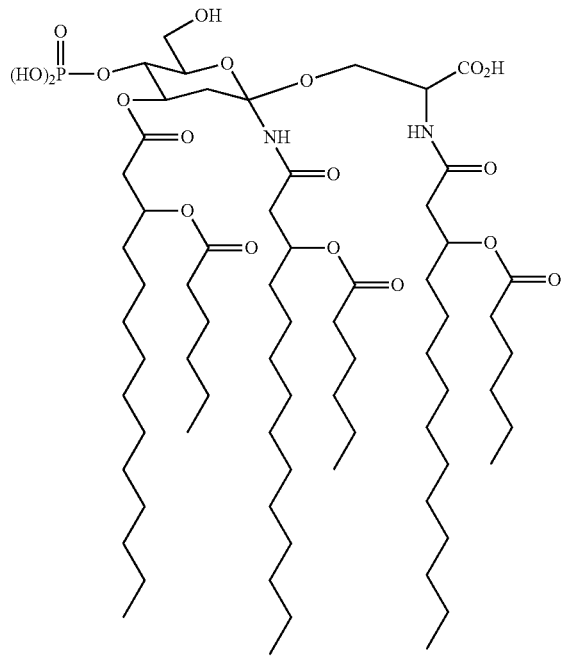

or a pharmaceutically acceptable salt or phosphate ester thereof. The above-identified TLR4 antagonist is commercially available from GlaxoSmithKline (UK) under the tradename CRX 526. (See Fort, Madeline M. et al. *Journal of Immunology*, 174: 6416-6423 (2005)).

In other embodiments, the TLR4 antagonist of formula (III) is a compound selected from one of the following:

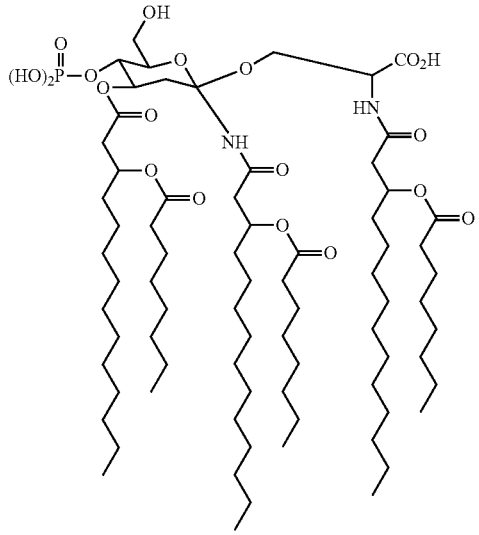

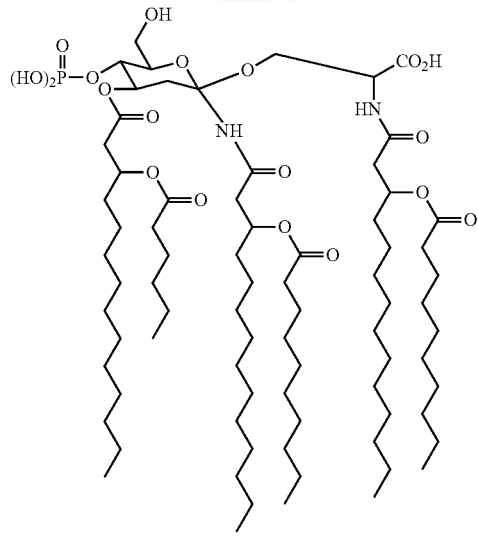

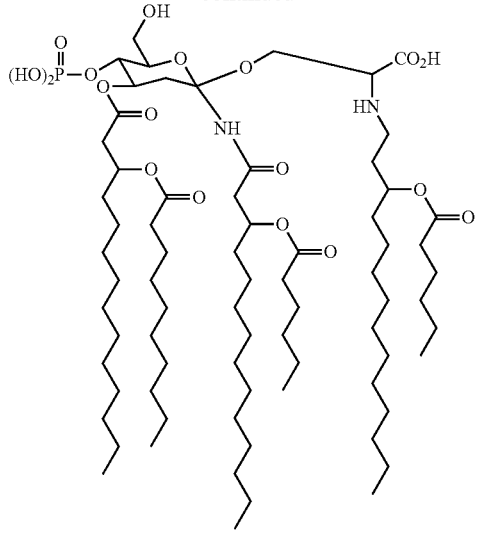

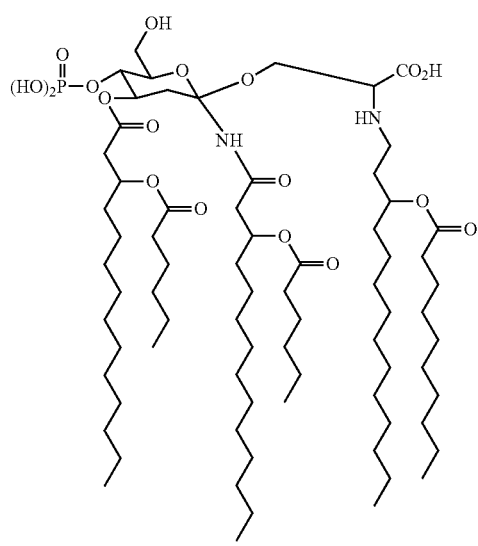

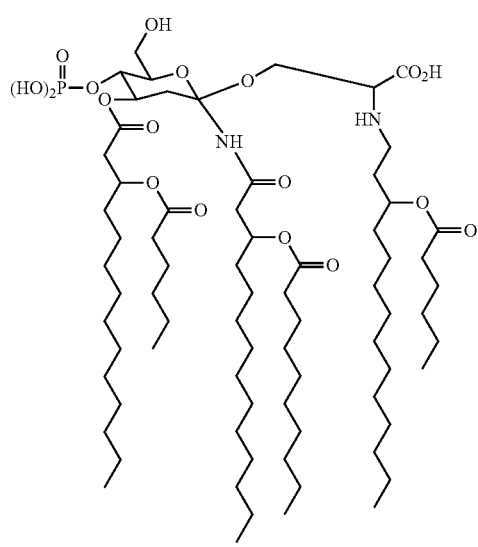

or pharmaceutically acceptable salts and phosphate esters thereof. The above identified examples of formula (III) are identified by Stover et al. (*Journal of Biological Chemistry* Vol. 27, No. 6) as being synthetic lipid A mimetics and were synthesized as described in Johnson et al. *Biorog. Med. Chem. Lett.* 9, 2273-2278.

In some embodiments, the TLR4 antagonist is a compound of formula (I):

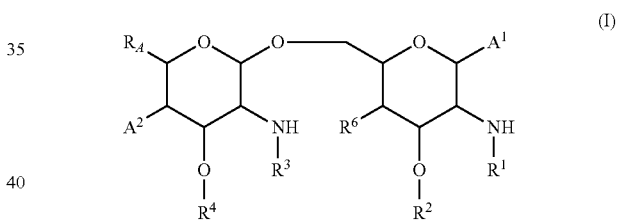

where $R^1$ is selected from the group consisting of:

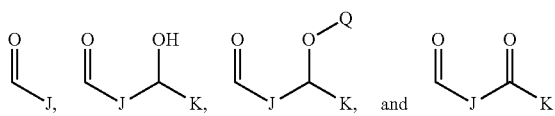

where each J, K, and Q, independently, is straight or branched C1 to C15 alkyl;

$R^2$ is straight or branched C5 to C15 alkyl;

$R^3$ is selected from the group consisting of straight or branched C5 to C18 acyl and

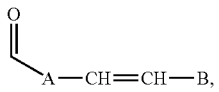

where A and B are each independently straight or branched C1 to C15 alkyl;

$R^4$ is selected from the group consisting of straight or branched C4 to C20 alkyl, and

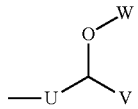

where each U and V, independently, is straight or branched C2 to C15 alkyl and W is hydrogen or straight or branched C1 to C5 alkyl;

$R_4$ is $R^5$—O—CH$_2$—, $R^5$ being selected from the group consisting of hydrogen, J', -J'-OH, -J'-O—K', -J'-O—K'—OH, and -J'-O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$ are each independently

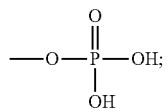

or a pharmaceutically acceptable salt or phosphate ester thereof.

In some embodiments, $R^1$ is

where J is straight or branched C10 to C15 alkyl.

In other embodiments, $R^1$ is

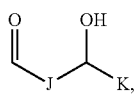

where J is straight or branched C1 to C3 alkyl and K is straight or branched C8 to C15 alkyl. In still other embodiments, $R^1$ is

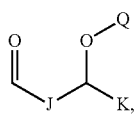

where J is straight or branched C1 to C3 alkyl, K is straight or branched C8 to C15 alkyl and Q is straight or branched C1 to C3 alkyl. In further embodiments, $R^1$ is

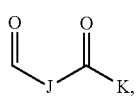

where J is straight or branched C1 to C3 alkyl and K is straight or branched C8 to C15 alkyl.

For example, in some embodiments, $R^1$ is

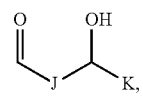

where J is —CH$_2$— and K is straight or branched C10 to C13 alkyl. In other embodiments, $R^1$ is

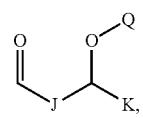

where J is —CH$_2$—, K is straight or branched C10 to C13 alkyl and Q is straight or branched —CH$_3$. In further embodiments, $R^1$ is

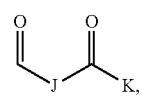

where J is —CH$_2$— and K is straight or branched C10 to C13 alkyl.

In some embodiments, $R^2$ is straight or branched C8 to C12 alkyl, e.g., straight or branched C10 alkyl. In some embodiments, $R^3$ is straight or branched C10 to C18 acyl, e.g., C18 acyl. In other embodiments, $R^3$ is

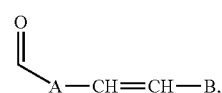

where A is straight or branched C7 to C12 alkyl and B is straight or branched C4 to C9 alkyl. For example, in some embodiments, $R^3$ is

where A is straight or branched C9 alkyl and B is straight or branched C6 alkyl.

In some embodiments, $R^4$ is straight or branched C8 to C12 alkyl, e.g., straight or branched C10 alkyl. In other embodiments, $R^4$ is

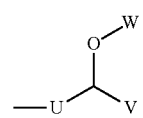

where U is straight or branched C2 to C4 alkyl, V is straight or branched C5 to C9 alkyl and W is hydrogen or —CH$_3$. For example, in some embodiments, $R^4$ is

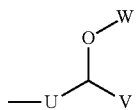

where U is straight or branched C2 alkyl, V is straight or branched C7 alkyl and W is hydrogen or —CH$_3$.

In some embodiments, R$_A$ is R$^5$—O—CH$_2$—, where R$^5$ is J' and where J' is straight or branched C1 to C5 alkyl. In some embodiments, R$_A$ is R$^5$—O—CH$_2$—, where R$^5$ is —CH$_3$.

In some embodiments, R$^6$ is hydroxyl.

In further embodiments, the TLR4 antagonist is a compound of formula (I):

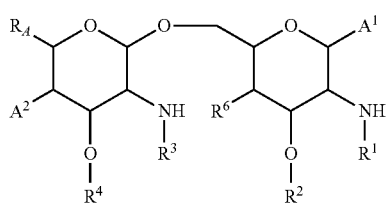
(I)

where R$^1$ is selected from

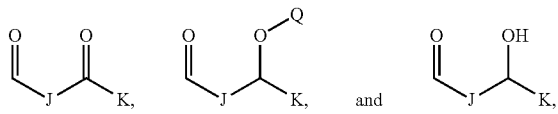

where J is straight or branched C1 to C3 alkyl, K is straight or branched C8 to C15 alkyl and Q is straight or branched C1 to C3 alkyl;
R$^2$ is straight or branched C8 to C12 alkyl
R$^3$ is

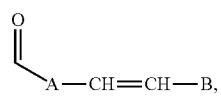

where A is straight or branched C7 to C12 alkyl and B is straight or branched C4 to C9 alkyl
R$^4$ is selected from straight or branched C8 to C12 alkyl and

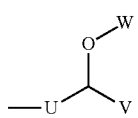

where U is straight or branched C2 to C4 alkyl, V is straight or branched C5 to C9 alkyl and W is hydrogen or —CH$_3$;
R$_A$ is R$^5$—O—CH$_2$—, where R$^5$ is J' and where J' is straight or branched C1 to C5 alkyl;
R$^6$ is hydroxyl;
A$^1$ and A$^2$ are each independently

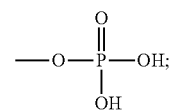

or pharmaceutically acceptable salt or phosphate ester thereof.

In still further embodiments, the TLR4 antagonist is a compound of formula (I):

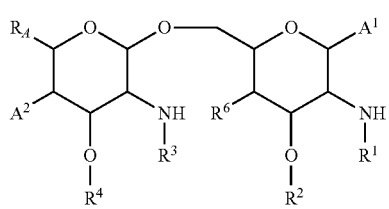
(I)

where R$^1$ is

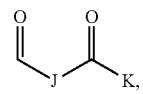

where J is straight or branched C1 to C3 alkyl, K is straight or branched C8 to C15 alkyl and Q is straight or branched C1 to C3 alkyl;
R$^2$ is straight or branched C8 to C12 alkyl
R$^3$ is

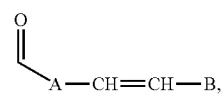

where A is straight or branched C7 to C12 alkyl and B is straight or branched C4 to C9 alkyl
R$^4$ is

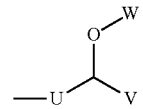

where U is straight or branched C2 to C4 alkyl, V is straight or branched C5 to C9 alkyl and W is hydrogen or —CH$_3$;
R$_A$ is R$^5$—O—CH$_2$—, where R$^5$ is J' and where J' is straight or branched C1 to C5 alkyl;
R$^6$ is hydroxyl;
A$^1$ and A$^2$ are each independently

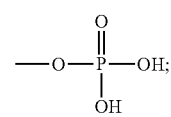

or pharmaceutically acceptable salt or phosphate ester thereof.

In another embodiment of the present invention, the TLR4 antagonist is a TLR4 polypeptide sequence, such as a polypeptide fragment of TLR4 that corresponds to at least a portion of the TLR4 receptor and binds TLR4 ligand during TLR4 signal transduction event. Other examples of TLR4 antagonists include a non-TLR4 protein or polypeptide that inhibits TLR4 activity, a small molecule inhibitor of TLR4 activity, or an inhibitory ligand that is a variant of the natural ligand of TLR4, namely bacterial lipopolysaccharide (e.g., analogs of the lipid A region of LPS as described above). Regardless of the type of TLR4 antagonist employed, the TLR4 antagonist can be administered to achieve at least transient blockade of TLR4 function, thereby neutralizing or at least partially inhibiting the effect of TLR4 on corneal inflammation.

In one example, the polypeptide fragment of TLR4 can include short polypeptides from about 10 to 100 or 10 to 50 amino acids in length (or smaller), which contain the TLR-4 ligand binding domain. These peptide fragments can also be part of an N-terminal or C-terminal fusion protein. The full length sequence of various human TLR4 isoforms are known (see Genbank Accession Nos. NP_6 12564 (isoform A), NP_6 12566 (isoform B), NP_003257 (isoform C), and NP_6 12567 (isoform D), each of which is hereby incorporated by reference in its entirety). Sequences for other mammalian TLR-4 homologs are also known, including those of mouse, rat, orangutan, etc.

Non-TLR4 protein or polypeptide inhibitors of TLR4 have also been identified in the literature, and these can be used in the methods and compositions of the present invention. Two such inhibitors are identified in Yang et al., "Novel TLR4 Antagonizing Peptides Inhibit LPS-Induced Release of Inflammatory Mediators by Monocytes," Biochem. Biophys. Res. Commun 329.3):846-54 (2005); and chemokine receptor 4 and its ligand have also been shown to be effective (Kishore et al., "Selective Suppression of Toll-like Receptor 4 Activation by Chemokine Receptor 4," FEBS Lett. 579(3): 699-704 (2005)).

Another example of a TLR4 antagonist that can be used in methods of the present invention is *Rhodobacter sphaeroides* lipid A (RSLA). RSLA has five acyl chains compared with six chains on Lipid A from most Gram negative bacteria, has pronounced antagonistic activity for other Gram negative Lipid A, and only minor agonist activity on some cell types (Kutuzova et al., *J. Immunol.* 2001; 167:482-489; Golenbock et al., *J. Biol. Chem.* 1991; 266:19490-19498; Qureshi et al., *Infection and Immunity* 1991; 59:441-444).

Other examples of TLR4 antagonists include, without limitation TAK-242 (Ii et al., "A Novel Cyclohexene Derivative, (TAK-242), Selectively Inhibits Toll-like Receptor 4-mediated Cytokine Production Through Suppression of Intracellular Signaling," Mo. Pharmacol. 69(4): 128 8-95 (2006); the endogenous TLR4 inhibitor RP1OS (Divanovic et al., "Inhibition of TLR4/MD-2 signaling by RP1O5/MD-1," J. Endotoxin Res. 11(6):363-368 (2005); CyP, a natural LPS mimetic derived from the cyanobacterium Oscillatoriaplanktothrix FP1 (Macagno et al., "A Cyanobacterial LPS Antagonist Prevents Endotoxin Shock and Blocks Sustained TLR4 Stimulation Required for Cytokine Expression," J. Exp. Med. 203 (6):1481-1492 (2006); a phenol/water extract from *T. socranskii* subsp. *socranskii* (TSS-P) (Lee et al., "Phenol/water Extract of *Treponema socranskii* subsp. *socranskii* as an Antagonist of Toll-like Receptor 4 Signaling," Microbiol. 1 52(2):535-46 (2006)); CLR proteins such as Monarch-i (Williams et al., "The CATERPILLER Protein Monarch-i Is an Antagonist of Toll-like Receptor-, Tumor Necrosis Factor alpha-, and *Mycobacterium tuberculosis*-induced pro-inflammatory signals," J. Biol. Chem. 280(48):39914-39924 (2005)); and small molecule TLR-4/TLR-2 dual antagonists, such as ER81 1243, ER81121 i, and ER81 1232 (U.S. Patent App. Pub. No. 20050113345 to Chow et al.). Further examples of TLR4 inhibitors or antagonists can be found in WO2006/138681A2.

The TLR4 antagonist used in methods of the present invention can be administered to the subject to treat corneal inflammation using standard methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the present methods of the invention can be altered, stopped, or re-initiated in a subject depending on the status of corneal inflammation. Treatment can be carried out as intervals determined to be appropriate by those skilled in the art. For example, the administration can be carried out 1, 2, 3, or 4 times a day. In another aspect of the present invention, a TLR4 antagonist can be administered after induction of the inflammatory response has occurred.

The methods of the present invention include administering to the subject a therapeutically effective amount of a TLR4 antagonist. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the TLR4 antagonist can be provided in ophthalmic preparation that can be administered to the subject's eye. The ophthalmic preparation can contain a TLR4 antagonist in a pharmaceutically acceptable solution, suspension, or ointment. Some variations in concentration can occur, depending on the particular TLR4 antagonist employed, the condition of the subject to be treated and the like, and the person responsible for treatment can determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5.

Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxymethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The TLR4 antagonists can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin include, for example, ointments, creams, gels and pastes comprising the TLR4 antagonist in a pharmaceutical acceptable carrier. The formulation of TLR4 antagonists for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with corneal inflammation (or at risk of corneal inflammation) which are not readily accessible or suitable for ophthalmic (e.g. eye-drops) and/or topical administration, can be treated by a systemic approach, such as intravenous infusion. For example, the TLR4 antagonist can be administered at a low dosage by continuous intravenous infusion. In another example, in which a patient requires longer-term care, the TLR4 antagonist can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the TLR4 antagonist to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the TLR4 antagonist.

The subjects to which TLR4 antagonists are administered can include mammals expressing TLRs on their cell membranes. More specifically, the subjects are mammals expressing TLRs on corneal epithelial cell, macrophage, and neutrophil membranes.

Subjects that are treated according to the methods of the present invention include those who have corneal inflammation. In addition, subjects who do not have, but are at risk of developing corneal inflammation can be treated according to the methods of the present invention. In the latter group of subjects, the treatment can inhibit or prevent the development of corneal inflammation in the subject.

In one aspect of the present invention, the corneal inflammation treated by the methods described herein are related to ocular disease or an ophthalmic disorder, such as uveitis, scleritis, episcleritis, keratitis, ocular or ophthalmic surgery (e.g., cornea surgery), endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, pterygium, and contact lens wear-induced conditions, such as a peripheral ulcer. In a more specific aspect of the present invention, the methods may be used to treat corneal inflammation related to microbial infection. In one specific example, keratitis may be caused by various microbial infections such as gram-negative bacteria *Pseudomonas aeruginosa* and *Serratia marcesans*, gram positive bacteria including *S. aureus, S. epidermidis* and *Corynebacterium* species (*P. acnes*). Therefore, in one aspect of the present invention the corneal inflammation inhibited in a subject is corneal inflammation associated with bacterial keratitis.

In another aspect of the invention, the methods described herein, can be used to treat corneal inflammation related to fungal keratitis. More specifically, the methods of the present invention can be used to treat corneal inflammation related to fungal genera including, for example, *Fusarium, Penicillium, Aspergillus, Cephalosporium* (*Acremonium*), *Trichophyton, Microsporum, Epidermophyton, Scopulariopsis,* and *Candida*.

In another aspect of the invention, the methods described herein can be used to treat sterile corneal inflammation in which no living organisms are recovered from either a contact lens or the corneal surface. More specifically, the methods of the present invention can be used to treat corneal inflammation in a subject associated with contact lens wear. These syndromes can include, but are not limited to Contact Lens Associated Corneal Infiltrates (CLACI), Contact Lens Associated Red Eye (CLARE), Contact Lens Peripheral Ulcer (CPLU). Sterile and infectious infiltrates can usually, but not always, be distinguished by slit lamp examination by those having ordinary skill in the art.

In yet another aspect, the TLR4 antagonists described herein can be administered as part of a combinatorial therapy with additional therapeutic agents. The phrase "combinatorial therapy" or "combination therapy" embraces the administration of a TLR4 antagonist, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, the combinational therapy can include the administration of a TLR4 antagonist with at least one anti-bacterial, antiviral or antifungal agent to treat corneal inflammation. Examples of anti-bacterials include Gentamycin, fortified with vancomycin for methicillin-resistant *Staphylococcus aureus* (MRSA) infections, $4^{th}$ generation fluoroquinoline like moxifloxacin or gatifloxacin, cefazolin or vancomycin and fluoroquinolone. In one specific example, the combinational therapy includes a TLR4 antagonist and at least one ophthalmic antibiotic or ophthalmic antiviral. Ophthalmic antibiotics include, for example, chloramphenicol sodium succinate ophthalmic (chlorphenical); CORTISPORIN (neomycin and polymyxin β sulfates and hydrocortisone acetate cream); ILOTYCIN (erythromycin ophthalmic ointment); NEODECADRON (neomycin sulfate-dexamethasone sodium phosphate); POLYTRIM (trimethoprim and polythyxin β sulfate ophthalmic solution); TERRA-CORTRIL (oxytetracycline HCL and hydrocortisone acetate); TERRAMYCIN (oxytetracycline); and TOBRADEX (tobramycin and dexamethosone ophthalmic suspension and ointment).

Ophthalmic antivirals include, for example, VIRA-A ophthalmic ointment, (vidarabine). Ophthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Ophthalmic sulfonamides include, for example, BLEPHAMIDE ophthalmic ointment (sulfacetamide sodium and prednisolone acetate); and BLEPHAMIDE ophthalmic suspension (sulfacetamide sodium and prednisolone acetate). Antifungals include, for example, natamycin and amphotericin-B.

The present invention further relates to a method of treating a TLR-induced inflammatory response in a subject's cornea. The method includes administering to the subject a therapeutically effective amount of a TLR4 antagonist. In one aspect of the present invention, the treatment of the TLR-induced inflammatory response can include the inhibition of cellular infiltrate into the subject's cornea. More particularly, the treatment of the TLR-induced inflammatory response can include the inhibition of neutrophil infiltrate into the subject's corneal stroma.

In another aspect of the present invention, the treatment of the TLR-induced inflammatory response can include the inhibition of CXC chemokine secretion, such as inhibition of interleukin-8 (IL-8). IL-8 is a CXC chemokine that can induce neutrophils to leave the bloodstream and enter into the surrounding tissue. Other CXC chemokines produced in the cornea and which have neutrophil activity include CXCL1, CXCL2, CXCL5, which can also be targeted by the methods of the present invention.

The present invention also relates to a contact lens for treating corneal inflammation in a subject. The contact lens includes a contact lens substrate and a coating provided on at least a portion of the substrate. The coating can include an amount of TLR4 antagonist effective to treat corneal inflammation in a subject upon administration of the contact lens to the subject.

Coatings including TLR4 antagonists can be applied to a number of contact lens substrate materials known in the art. Virtually any substrate known in the art that can be fashioned into a contact lens can be used in the present invention provided it is optically transparent.

In an aspect of the invention, the substrate can include optically transparent materials that allow oxygen to reach the cornea in an amount, which is sufficient for long-term corneal health. Examples of substrates include polymers made from hydrophobic materials, such as silicone copolymers, interpolymers, oligomers, and macromers. Illustrative polysilicones are polydimethyl siloxane, polydimethyl-co-vinylmethylsiloxane. Other silicones include silicone rubbers described in U.S. Pat. No. 3,228,741 to Becker; blends such as those described in U.S. Pat. No. 3,341,490 to Burdick et al., and silicone compositions such as described in U.S. Pat. No. 3,518,324 to Polmanteer. Substrates described in U.S. Pat. Nos. 4,136,250; 5,387,623; 5,760,100; 5,789,461; 5,776,999; 5,849,811; 5,314,960 and 5,244,981 can also be used in the invention. Cross-linked polymers of propoxylate of methyl glucose and propylene oxide and HEMA-based hydrogels can also be used as substrates of the contact lens.

Silicone compositions that can be used in forming the contact lens of this invention are the cross-linked polysiloxanes obtained by cross-linking siloxane prepolymers by means of hydrosilylation, co-condensation and by free radical mechanisms such those described by Chen in U.S. Pat. No. 4,143,949, which is incorporated herein by reference. Additional silicone-based substrates are cross-linked polymers of α,ω-bisamionpropyl polydimethylsiloxane, and gylycidyl methacrylate, cross-linked polymers. Silicone compositions also contemplated by the present invention are made from combining a methacrylate with one or more silicone monomers in the presence of a group transfer polymerization (GTP) catalyst to form a macromer that is subsequently polymerized with other monomers to give the final substrate. Initiators, reaction conditions, monomers, and catalysts that can be used to make group transfer (GTP) polymers are described in "Group Transfer Polymerization" by O. W. Webster, in Encyclopedia of Polymer Science and Engineering Ed. (John Wiley & Sons) p. 580, 1987. Substrates described in U.S. Pat. No. 6,951,894 are also suitable for use in the present invention.

The coating can be prepared and applied as an aqueous solution, suspension, or colloid and then applied to the contact lens substrate according to any process that can provide the coating in contact with the substrate. For example, process for applying the coating to the substrate include immersion, spraying, brushing, and spin coating. Once the lens substrate is coated it may be subjected to any number of additional steps that are conducted in the manufacture of contact lenses. These can include, for example, swelling and washing steps, the addition of additives such as surfactants, extraction steps and the like.

The coating including the TLR4 antagonist can adhere to the contact lens by, for example, chemical bonding, such as covalent or ionic bonding, or physical bonding. In some aspects, the coating can remain affixed to the lens substrate throughout its useful life (e.g., storage time plus the time in which it will be in contact with a user's eye).

The contact lens can also include more than one layer of coating. This can be desirable where the coating layer will provide the requisite surface properties (e.g. treatment of corneal inflammation) but is not particularly compatible with the lens substrate itself. For example, a tie-layer or coupling agent can be used to adhere the coating to the substrate. Selections of compatible lens substrate, TLR4 antagonist coating, and tie-layer (if necessary) materials is well within the knowledge of one skilled in the art.

In aspect of the invention, the contact lens is non-toxic to the subject's cornea and other tissue while providing for the treatment of corneal inflammation in the subject.

The present invention also relates to an ophthalmic solution for treating corneal inflammation in a subject. The solution can be aqueous and include a TLR4 antagonist as described above. Examples of solutions useful that can be used in the treatment of corneal inflammation include solutions that are contacted with eye lids and/or eyes, such as multipurpose lens solutions, opthalmalic rinse solutions, surgical scrubs for eye use, eye drops, eye wash solutions, contact lens solutions, topical over the counter ocular and periocular solutions (i.e. artificial tears), ocular and periocular cleaning solutions, eye irrigating solutions, and/or antibacterial solutions for surgical scrubs or topical application.

In some aspects, a TLR4 antagonist may be added to a commercially available contact lens solution or a multipurpose lens solution to treat corneal inflammation. In other aspects, a TLR4 antagonist may be added to an aqueous solution prepared for use as a contact lens or multipurpose lens solution that is not commercially available to treat corneal inflammation.

In some aspect where the ophthalmic solution includes a cleaning solution, the cleaning solution can include cleaning agents to effectively clean a lens of film deposits and surface debris. Examples of cleaning agents that can be used include, poloxamers and tetronic surfactants comprising poly(oxythylene)hydrophilic units. In all embodiments, the cleaning agents are nontoxic, and do not distort the vision of the subject being treated for corneal inflammation.

In other aspects, TLR4 antagonists may be added to tonicity agents and buffers that are found in conventional ophthalmic solutions. Examples of tonicifiers include dextrose, potassium chloride and/or sodium chloride. Examples of buffers include boric acid, sodium borate, sodium or potassium citrate, sodium bicarbonate, sodium phosphate, and potassium phosphate.

Additionally, antibacterial agents found in conventional ophthalmic solutions, such as multipurpose lens solutions, may be added. Antibacterial agents for use in the solution include, for example, polyaminopropyl biguanide, alexidine hydrochloride, polyquaternium-1, polyquaternium 42, myristamidopropyl dimethylamine, or other agents known to those skilled in the art.

In some aspects, the solution may further include a comfort or moisturizing agent to provide hydration and lubrication of a subject's contact lens. Such agents include, for example, polyquaternium 10, poloxamer, propylene glycol, hydroxypropylmethylcellulose (HPMC), or other agents known to those skilled in the art.

Since, in some aspects, the solution is intended to be administered topically to the eyelids and/or eye, it is contemplated that the solution be free of pathogenic organisms and/or sterile. A benefit of a sterile solution is that it reduces the possibility of introducing contaminants into a subject's eyelids and/or eye. Sterility or adequate antimicrobial preservation may be provided as part of the present solutions of the present invention. In some aspects, the solutions are produced under sterile conditions.

In addition to or in place of sterilization, aqueous solutions of the TLR4 antagonist may contain a physiologically acceptable preservative to minimize the possibility of microbial contamination. A physiologically acceptable preservative may be used in the solutions of the present invention to increase the stability of the solutions. Preservatives include, for example, polyaminopropyl biguanide, polyhexamethylene biguanide (PHMB), polyquaternium-1, myristamidopropyl, and sorbic acid.

The invention is further illustrated by the following example, which is not intended to limit the scope of the claims.

EXAMPLES

In the following examples, C57BL/6 mouse corneas were abraded and treated with eritoran tetrasodium or placebo prior to, or following stimulation with LPS or the TLR2 ligand Pam3Cys. A 2 mm punch from a soft contact lens was used to cover the corneal surface throughout the inhibition and stimulation period. Corneal infiltrates were detected by in vivo confocal microscopy (CONFOSCAN) and by immunohistochemistry for neutrophils. The effect of eritoran tetrasodium on IL-8 production by LPS and Pam3Cys stimulated human corneal epithelial cells (HCEC), macrophages and neutrophils was also assessed.

As illustrated in the examples below, we observed that eritoran tetrasodium significantly inhibited CXC chemokine production in the cornea and development of corneal infiltrates, specifically neutrophils, in response to stimulation with LPS (TLR4), but not Pam3Cys (TLR2). When eritoran tetrasodium was applied following LPS stimulation, neutrophil infiltration was significantly inhibited, although a higher concentration was needed. Furthermore, IL-8 production by TLR4-but not TLR2 stimulated HCEC, macrophage and neutrophil cell lines was also significantly reduced.

We also observed that eritoran tetrasodium is a highly effective antagonist of LPS-induced corneal infiltrates associated with contact lenses, even if given after induction of the inflammatory response. Although specific for TLR4, eritoran tetrasodium is shown here to inhibit LPS-induced IL8 production in several cell types.

Example 1

Eritoran Tetrasodium Preparation

Eritoran tetrasodium and Placebo were obtained from Eisai Research Institute, Andover, Mass., and reconstituted at 1.1 mg/ml in endotoxin free water (Sigma; UK). This stock reagent was aliquotted and stored at −80° C. Samples were sonicated prior to diluting to the concentrations noted for each experiment.

Example 2

Cell Lines and In Vitro Stimulation

The SV-40 transfected human corneal epithelial cell line (HCE-T) was obtained from ATCC. Before stimulation, HCE cells were plated into 48 well plates and underwent epidermal growth factor starvation overnight. As HCE cells require exogenous MD-2 to respond to LPS, cells were incubated 1 h with 200 ng/ml recombinant human MD-2 (R&D Systems, Minneapolis, Minn.) prior to stimulation with ultrapure LPS (TLR4-specific, *Escherichia coli* K12, Invivogen; San Diego, Calif.). HCE cells were also incubated with Pam3CysK4 (EMC Microcollections, Germany) in the absence of MD-2.

The U937 macrophage-cell line was cultured in RPMI medium (GIBCO) with 10% FBS, and $5 \times 10^4$ cells/well were added to 96-well plates. The human neutrophil-like cell line (HL-60) was maintained in RPMI with 10% FBS, and incubated five days in 1.2% DMSO to generate the neutrophil phenotype.

All cells were incubated with eritoran or placebo, followed by stimulation with LPS or Pam3CysK4 at optimal concentrations for each cells line (noted in results). After 3 h, cell-free supernatants were collected, and CXCL8/IL-8 was measured by ELISA (R&D Systems).

The results are shown in FIGS. 2, 3, and 14-19.

Example 3

Mouse Model of Contact Lens Corneal Inflammation

C57BL/6 mice (6-8 weeks old) were obtained from The Jackson Laboratory (Bar Harbor, Me.). Mice were anesthetized by intraperitoneal injection of 0.4 ml 2,2,2-tribromoethanol (TBE). A 26 gauge needle was used to make three parallel abrasions in the corneal epithelium as described in our previous studies. Eritoran tetrasodium or placebo at concentrations indicated for each experiment was added topically, and a 2 mm diameter punch from a normal contact lens (LOTRAFILCON A; CIBA VISION) was added to the corneal surface (See FIG. 1). After an additional 1 h, the lens was briefly removed, and 2 µl LPS (20 mg/ml) or $Pam_3Cys$ (5 mg/ml) was placed on the corneal surface. The contact lens button was then replaced, and after an additional 1 h, the lens was removed and the mice were allowed to recover from anesthesia. In some experiments, the order of agonist and antagonist was reversed, or both were given simultaneously.

Example 4

*Pseudomonas aeruginosa*-Induced Corneal Inflammation

*Pseudomonas aeruginosa* strain ATCC 19660 was obtained directly from ATCC and maintained in stocks at −80° C. Bacteria were grown overnight (18 hours) in tryptic soy broth (TSB), and aliquots from these stationary cultures were diluted 1:100 and grown in TSB until $OD_{650}$=0.2 ($1 \times 10^8$ CFU/mL). The bacteria were centrifuged, washed in PBS, and resuspended at $2 \times 10^9$ bacteria/mL in 0.3% tobramycin in PBS (Sigma-Aldrich). Bacterial killing was confirmed by absence of growth on TSB agar plates. The corneas were abraded by three parallel scratches, and a 5-µL bacterial suspension containing $1 \times 10^7$ organisms was placed on the corneal surface and covered by a 2-mm diameter punch from a silicon hydrogel contact lens (Lotrafilcon; Ciba Vision), as just described.

Example 5

In Vivo Confocal Microscopy Analysis of Corneal Thickness and Haze

In vivo analysis of cellular infiltration was accomplished using a NIDEK CONFOSCAN. Mice were anesthetized and immobilized, and the cornea was examined using a 40× objective with a transparent gel (Genteal, Novartis Ophthalmics, Duluth, Ga.) as a medium. A series of images of the entire cornea was captured using NAVIS software, and stromal thickness (area between basal epithelium and corneal endothelium) was measured directly using the NAVIS software. To measure total infiltrate (termed corneal haze), the light intensity readout of each 1-2 µm image of the corneal stroma was exported into Prism (Graph Pad Software, San Diego, Calif.), and the total area under the curve was then calculated as previously described. (Sun Y et al. *Infection and immunity* 2006; 74:5325-5332; Johnson A C et al. *Invest Ophthalmol V is Sci* 2005; 46:589-595).

Example 6

Immunohistochemistry

Eyes were snap frozen in liquid nitrogen, and 5 µm sections were incubated 2 h with anti-neutrophil antibody NIMP-R14 diluted to 2 µg/ml in 1% fetal calf serum/TBS (1% FCS/TBS). After washing, corneal sections were incubated with FITC-conjugated rabbit anti-rat antibody (Vector Laboratories, Burlingame, Calif.) diluted 1:200 from stock in 1% FCS/TBS. Slides were mounted in Vectashield containing DAPI (Vector Laboratories), and the number of neutrophils in each section was examined by fluorescence microscopy and quantified by direct counting.

Example 7

Apoptosis Assay

The cell viability in vitro was measured by trypan blue. The corneal sections were incubated with terminal deoxynucleotidyl transferase-mediated dUTP nick end labeling (TUNEL) reagents according to manufacturer's directions (Roche, Penzberg, Germany), and the number of TUNEL positive cells in the cornea was quantified by fluorescence microscopy.

Example 8

Statistics

Statistical analysis was performed using an unpaired t-test (Prism; Graph Pad Software, San Diego, Calif.). A p value of less than 0.05 was considered significant.

Example 9

Effect of Eritoran Tetrasodium on LPS-Induced CXC Chemokine Production in the Cornea The role of eritoran tetrasodium in LPS-induced corneal inflammation was determined using a model of contact lens corneal inflammation described in Example 3. Briefly, Corneas of C57BL/6 mice were abraded with three parallel, superficial scratches. 2 µl of 350 mg/ml Eritoran or placebo was added topically, and a 2 mm diameter punch from a soft contact lens was placed on the corneal surface as shown in FIG. 1. After 1 h, the lens was removed, 2 µl LPS (20 mg/ml) or $Pam_3Cys$ (5 mg/ml) was added topically, and the lens was replaced. After 1 h, the lens was removed, and 3 h later (4 h after stimulation), and corneas were dissected, homogenized, and CXCL1/KC was measured by ELISA.

Figure 2:
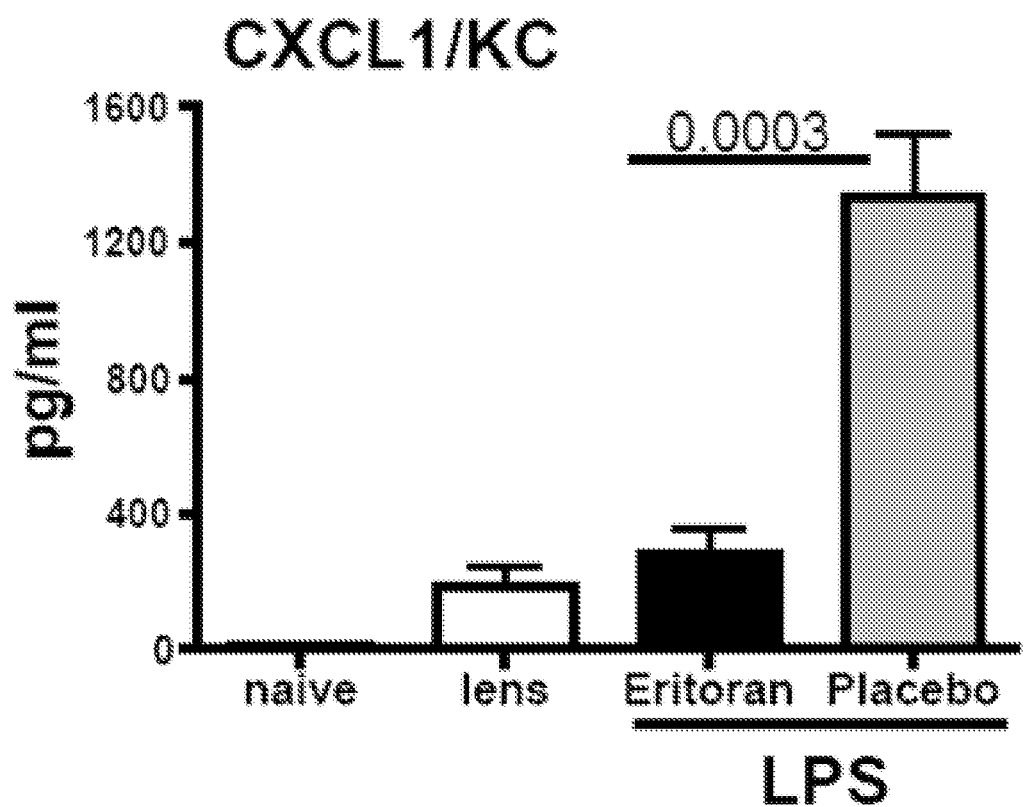
FIG. 2 illustrates a graph comparing chemokine production from LPS-stimulated corneas treated with eritoran tetrasodium (E) (E5564) or placebo (P).

FIG. 2 shows that CXCL1/KC in LPS-stimulated corneas was significantly inhibited by Eritoran compared with placebo (p=0.003). However, in the presence of LPS (and placebo), CXCL1/KC was elevated significantly. However, when corneas were pre-treated with eritoran tetrasodium prior to LPS, chemokine production was ablated, demonstrating the antagonistic effect of eritoran tetrasodium in this model.

Figure 3:
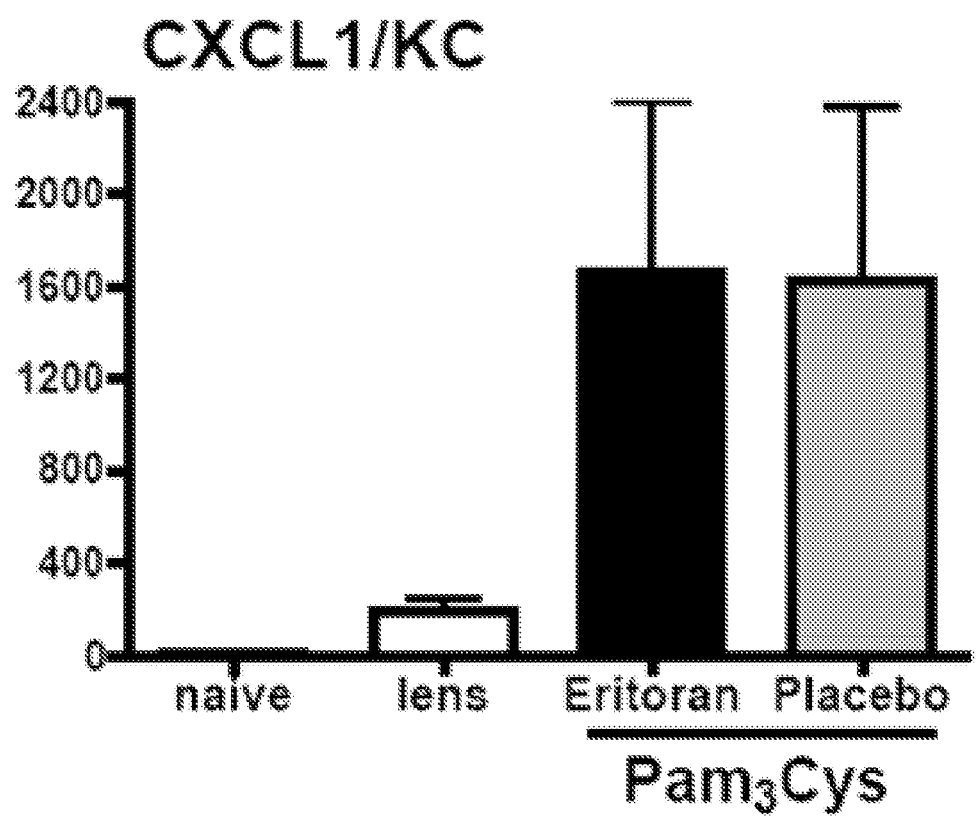
FIG. 3 illustrates a graph comparing chemokine production from Pam3Cys stimulated corneas, eritoran treated corneas (E), and placebo groups (P).

We treated corneas with eritoran tetrasodium prior to stimulation with Pam3Cys to determine specificity of eritoran tetrasodium. FIG. 3 shows that in CXCL1/KC in $Pam_3$ Cys-stimulated corneas there was no difference between Eritoran and placebo. This experiment is representative of two repeat studies with five mice per group.

Example 10

Effect of Eritoran Tetrasodium on Cellular Infiltration of the Corneal Stroma

There was no effect of eritoran tetrasodium on Pam3Cys/TLR2-induced corneal inflammation (FIG. 2, bottom panels), further demonstrating the selective effect of this antagonist.

Example 11

Figure 4:
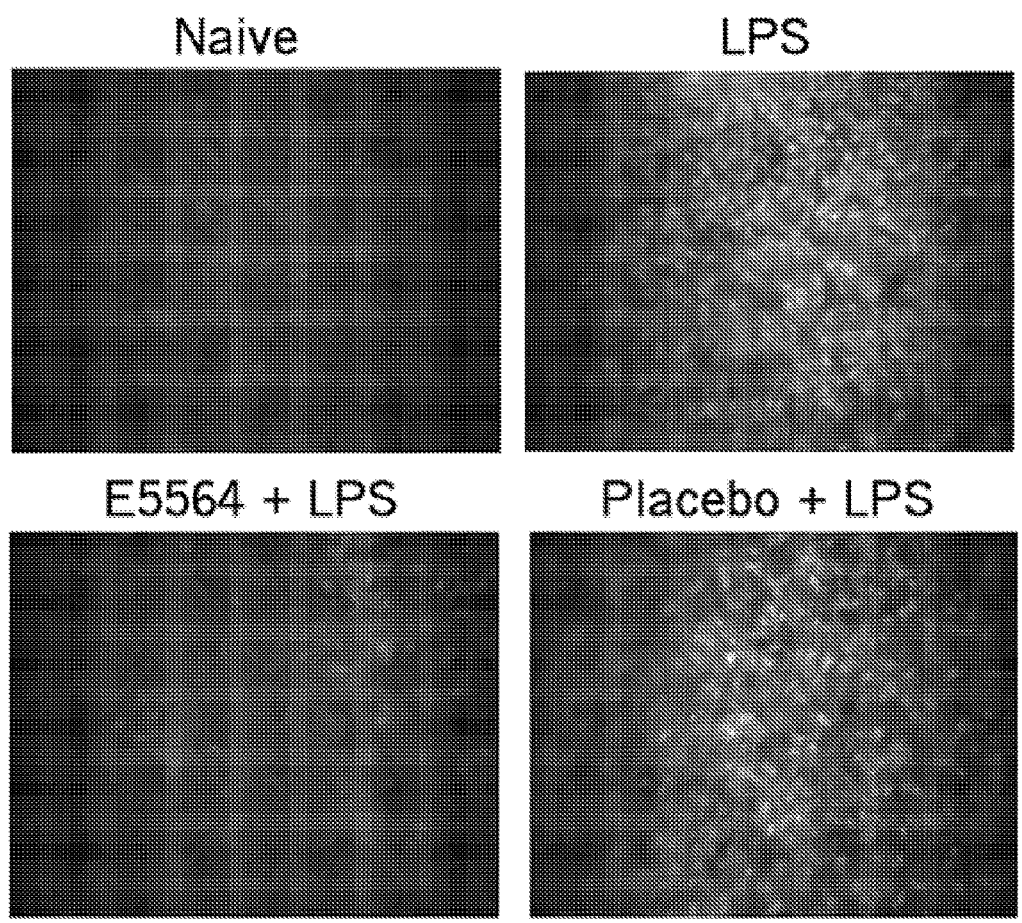
FIG. 4 illustrates confocal microscopy images of the central cornea stimulated with LPS, eritoran tetrasodium (E) and LPS, and Placebo and LPS.

Effect of Eritoran Tetrasodium on Cellular Infiltrate into the Central Corneal Stroma To determine the effect of eritoran tetrasodium on cellular infiltration, corneas were abraded and treated with eritoran tetrasodium or placebo with a contact lens as described in Example 3, above. After 2 h, the contact lens were removed, and after 24 h, which is the peak of neutrophil infiltration, corneas were examined by in vivo confocal microscopy (CONFOSCAN), and images of the central cornea were captured. The in vivo confocal microscopy images are shown in FIG. 4. The images of FIG. 4 show that there were no infiltrating cells in corneas of naïve mice, whereas LPS treated corneas showed an intense cellular infiltrate in the central corneal stroma (detected as small, light reflective cells) 24 h after contact lens associated exposure to LPS either alone or in the presence of placebo. In marked contrast, we observed that corneas treated with eritoran tetrasodium prior to LPS showed minimal cellular infiltrate in the central corneal stroma, indicating that eritoran tetrasodium pre-treatment inhibits cellular infiltration to the corneal stroma in this model of corneal inflammation.

Example 12

Effect of Pre-Treatment with Eritoran Tetrasodium on LPS-Induced Contact Lens-Associated Neutrophil Recruitment and Development of Corneal Haze Corneas were treated using a model of contact lens corneal inflammation as discussed in Example 3, above, and as shown in FIG. 1. We then quantified the inhibitory effect of eritoran tetrasodium on cellular infiltrates to the cornea after 24 h by measuring reflectivity in the corneal stroma in accordance with Example 4. Each 1 μm section from anterior to posterior stroma was measured in terms of light reflectivity. These measurements were used to generate a curve. The area under curve represents the total infiltrate. The number of neutrophils per corneal section was then directly counted.

Figure 5:
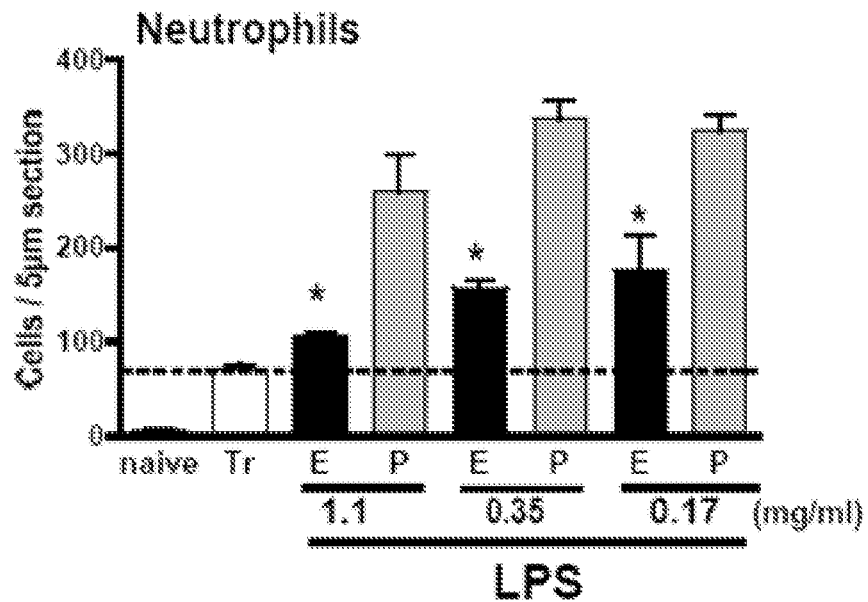
FIG. 5 illustrates a graph comparing neutrophil infiltrate in LPS-stimulated corneas for different dose responses for mice treated with eritoran tetrasodium (E) or placebo (P).
Figure 6:
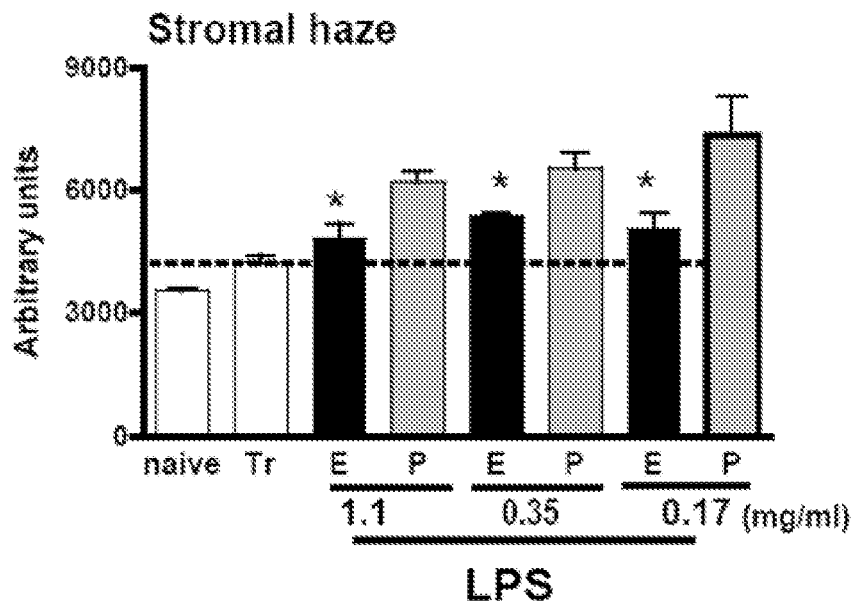
FIG. 6 illustrates a graph comparing stromal haze in LPS-stimulated corneas for different dose responses for mice treated with eritoran tetrasodium (E) or placebo (P).

FIGS. 5 and 6 show corneas that were abraded and incubated with contact lenses alone had approximately 50 neutrophils per section, whereas LPS-treated corneas had greater than 300 neutrophils/corneal section. Mice given topical application of eritoran tetrasodium prior to LPS had a dose-dependent reduction in neutrophil numbers, with 0.35 mg/ml needed to reduce neutrophil numbers by 50%. Trauma controls (Tr) were abraded corneas exposed only to saline and incubated 2 h with a contact lens. Significant differences ($p<0.05$) between Eritoran and placebo are indicated by an asterisk. Repeat experiments showed that 0.35 mg/ml was the minimum inhibitory concentration.

Figure 7:
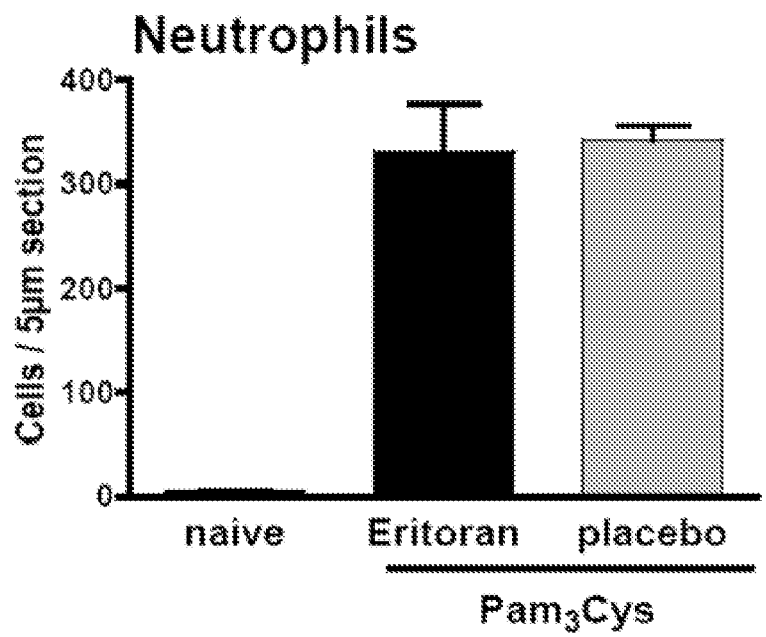
FIG. 7 illustrates a graph comparing neutrophil infiltrate in Pam3Cys-stimulated corneas for different dose responses for mice treated eritoran tetrasodium (E) or placebo (P).
Figure 8:
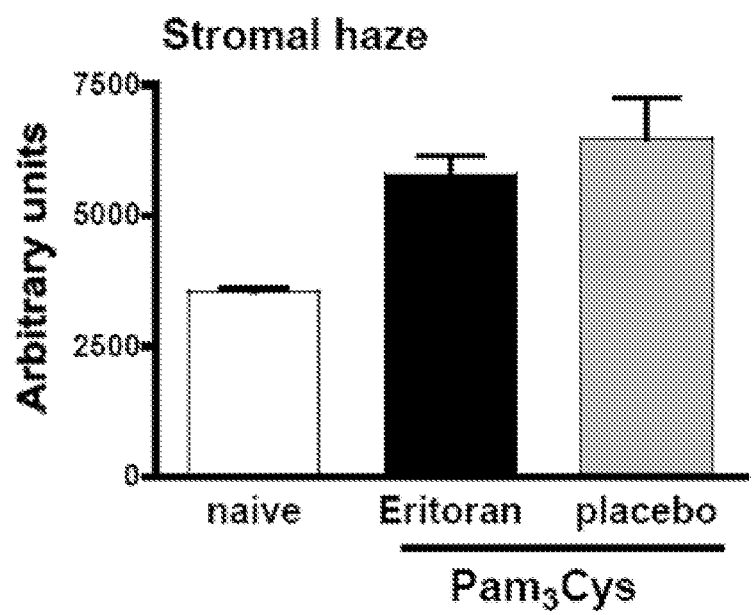
FIG. 8 illustrates a graph comparing stromal haze in Pam3Cys-stimulated corneas for different dose responses for mice treated with eritoran tetrasodium (E) or placebo (P).

FIGS. 7 and 8 show neutrophil infiltration and reflectivity in corneas stimulated with Pam3Cys. TLR2 activation induced neutrophil infiltration and development of corneal haze. Pretreatment with the highest concentration of eritoran tetrasodium had no effect on either neutrophil infiltration or total reflectivity. Taken together, these findings demonstrate that eritoran tetrasodium has a dose dependent antagonistic effect on TLR4- and not TLR2-induced corneal inflammation.

Example 13

Effect of Eritoran Tetrasodium Applied Following LPS-Induced Corneal Inflammation To determine if eritoran tetrasodium can inhibit corneal inflammation after the response has been initiated, corneas were abraded and stimulated with LPS as described above. We added eritoran tetrasodium 1 h after LPS stimulation. This protocol was performed in parallel with mice either pre-treated with eritoran tetrasodium, or mice given eritoran tetrasodium and LPS simultaneously. Neutrophil infiltration and corneal haze were examined as before and the results are shown in FIGS. 9-12.

Figure 9:
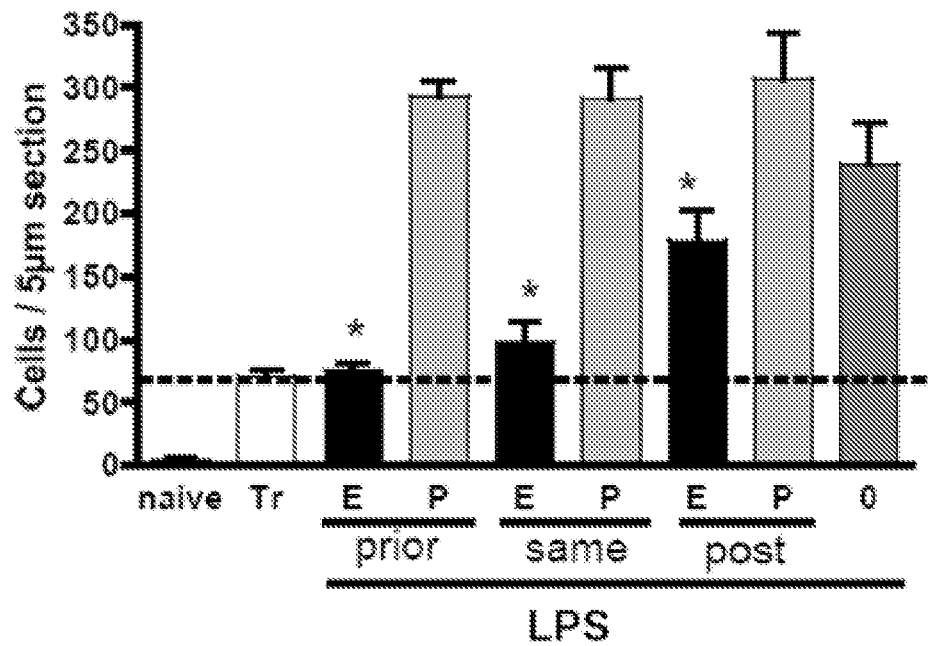
FIG. 9 illustrates a graph comparing neutrophil infiltrate in corneas for different dose responses for mice treated eritoran tetrasodium (E) or placebo (P) before and after LPS stimulation.
Figure 10:
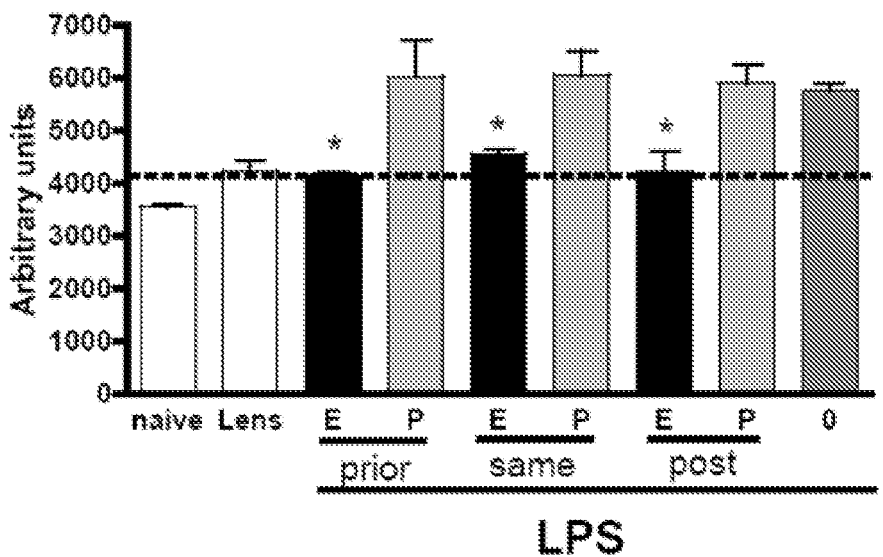
FIG. 10 illustrates a graph comparing stromal haze in corneas for different dose responses for mice treated eritoran tetrasodium (E) or placebo (P) before and after LPS stimulation.
Figure 11:
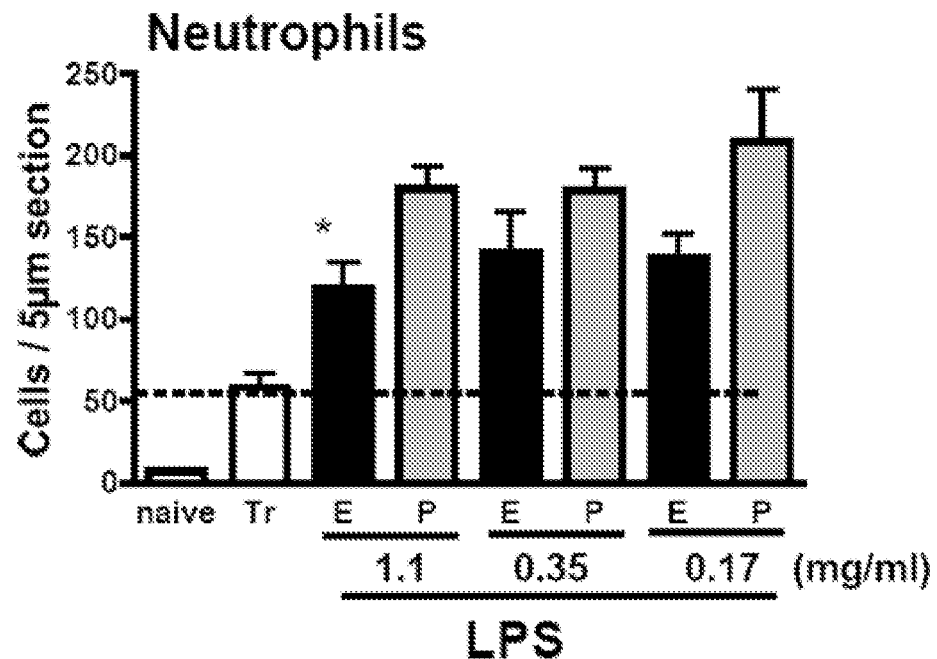
FIG. 11 illustrates a graph comparing the dose response for treating neutrofil infiltrate in corneas with eritoran tetrasodium after LPS stimulation.
Figure 12:
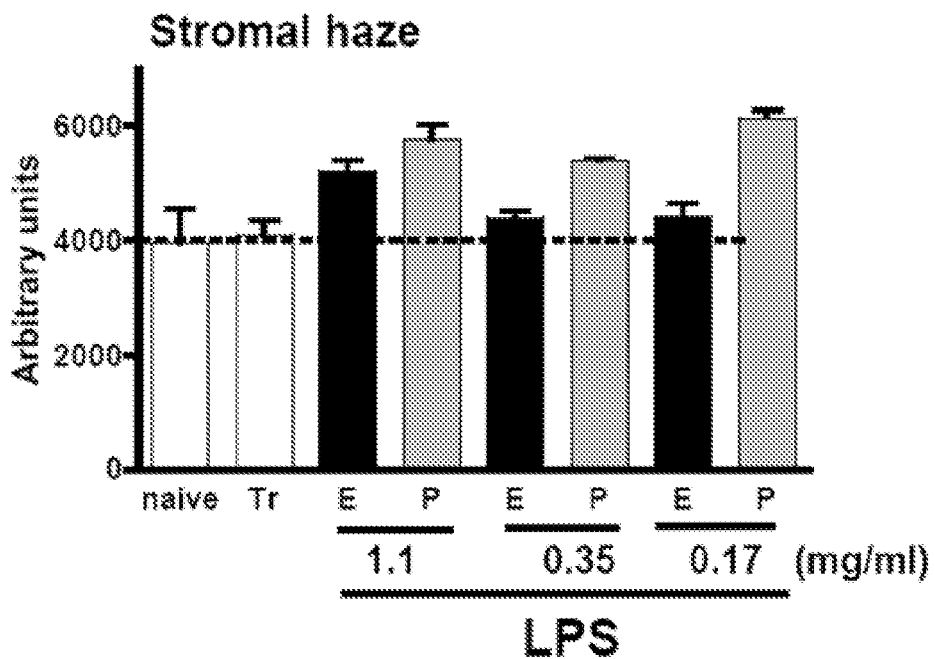
FIG. 12 illustrates a graph comparing the dose response for treating stromal haze in corneas with eritoran tetrasodium after LPS stimulation.

FIGS. 9 and 10 show LPS-induced neutrophil infiltration and corneal haze were significantly reduced in all eritoran tetrasodium groups compared with placebo, indicating that antagonism remains effective even after the inflammatory response has been initiated. In some experiments, eritoran tetrasodium was applied again after 3 h (when the contact lens was no longer present), but there was no significant difference between this and the single eritoran tetrasodium treatment. FIGS. 11 and 12 show the dose response for treating eritoran tetrasodium after LPS stimulation. Asterisks denote significant differences ($p<0.05$) between Eritoran and placebo. Note that neutrophil numbers were significantly lower in each protocol, whereas concentrations lower than 1.1 mg/ml had no significant effect. These experiments were repeated three times with similar results.

Example 14

Effect of Eritoran Tetrasodium on Apoptosis in the Corneal Epithelium

Figure 13:
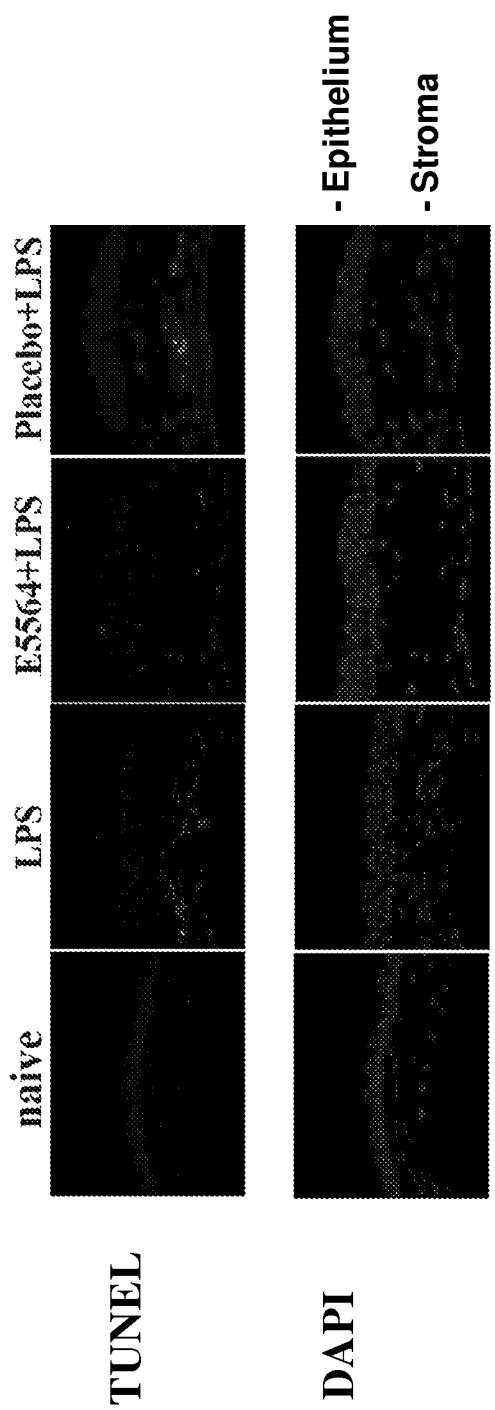
FIG. 13 illustrates eritoran tetrasodium (E) or placebo (P) treated LPS-stimulated mice cornea sections stained using a terminal deoxynucleotidyl transferase dUTP nick end labeling (TUNEL) assay, and counterstained with 4',6-diamidino-2-phenylindole (DAPI) to identify individual cells.

The experiment in Example 7 was conducted to determine if eritoran tetrasodium has a pro-apoptotic effect on the corneal epithelium. Mice were pre-treated with 2.2 μg eritoran tetrasodium prior to LPS, as described above, and eyes were snap frozen. We used a TUNEL assay on 5 μm corneal sections to identify apoptotic cells. Total cells were identified using DAPI. As shown in FIG. 13, we observed no TUNEL positive cells in the corneal epithelium in which eritoran tetrasodium was applied, either in the presence or absence of LPS. We detected TUNEL positive cells in the corneal stroma of LPS treated corneas, either alone or with placebo, which corresponds to the presence of neutrophils (not shown). These observations indicate that there is no pro-apoptotic effect of eritoran tetrasodium in this model.

Example 15

Effect of Eritoran Tetrasodium on LPS-Induced IL-8 Production by Human Corneal Epithelial Cells, Macrophages and Neutrophils As Example 10 indicated that eritoran tetrasodium has an inhibitory role in vivo, we next examined the effect of eritoran tetrasodium on LPS-induced production of the CXC chemokine IL-8 by specific cell types in the cornea. The normal mammalian corneal epithelium comprises an external multilayer of corneal epithelial cells that can respond to TLR ligands, resident macrophages and dendritic cells that express TLRs, and neutrophils. We utilized representative cell lines.

Figure 14:
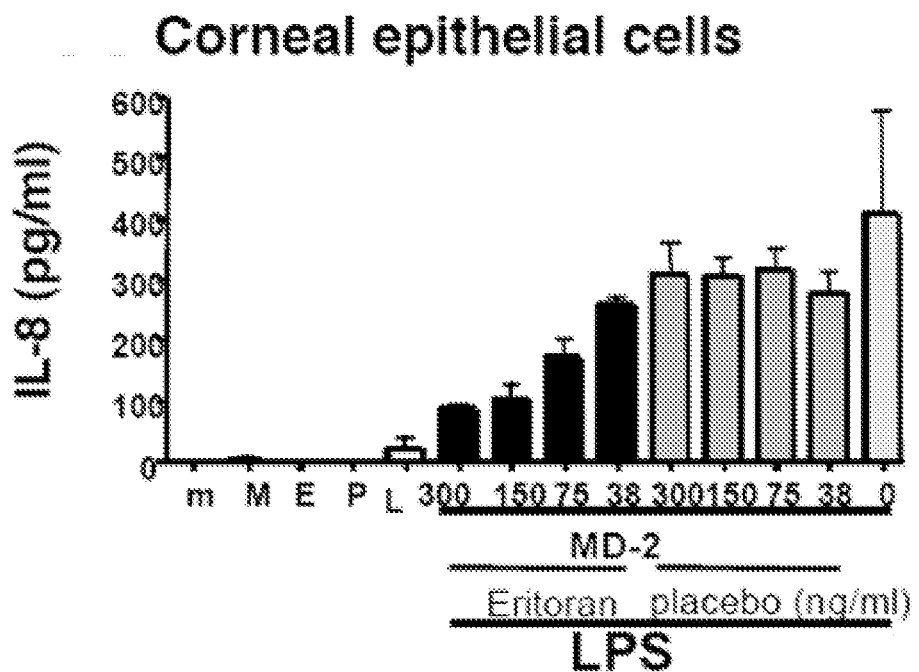
FIG. 14 illustrates a graph showing the IL-8 levels in the culture supernatant of human corneal epithelial cells (HCE-T) stimulated with LPS in the presence of eritoran tetrasodium (E) versus placebo (P) after 24 hours.
Figure 15:
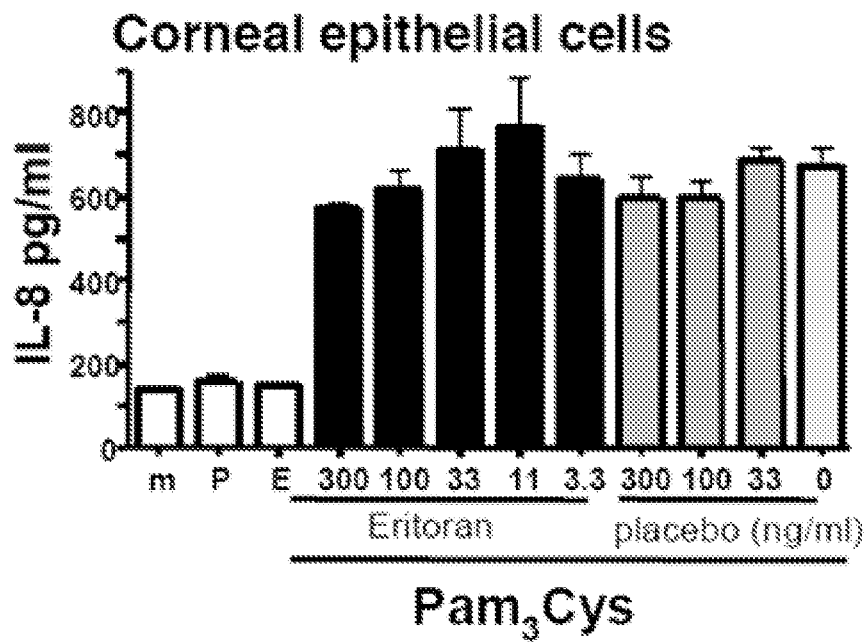
FIG. 15 illustrates a graph showing the IL-8 levels in the culture supernatant of human corneal epithelial cells (HCE-T) stimulated with Pam3cys in the presence of eritoran tetrasodium (E) versus placebo (P) after 24 hours.
Figure 16:
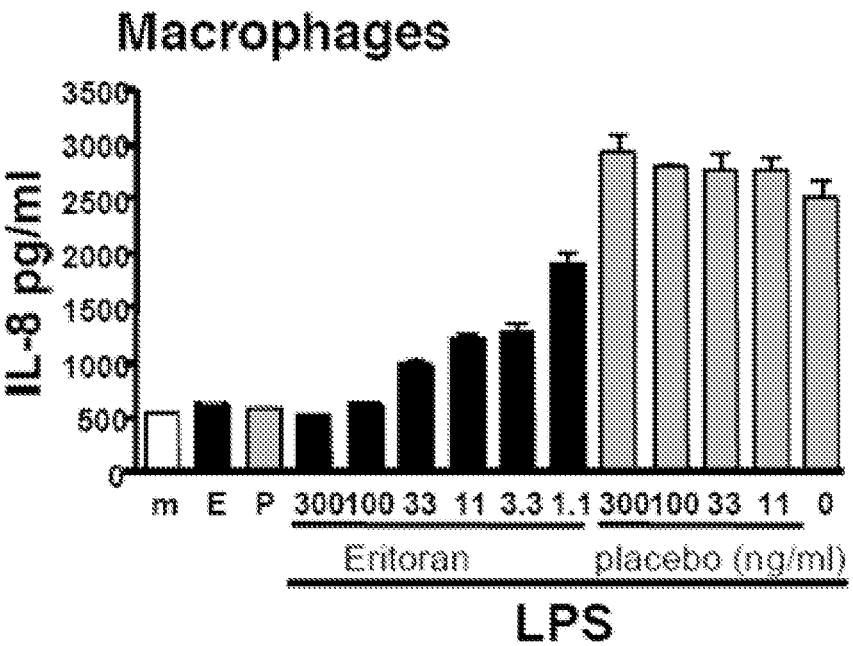
FIG. 16 illustrates a graph showing the IL-8 levels in the culture supernatant of macrophages (U937) stimulated with LPS in the presence of eritoran tetrasodium (E) versus placebo (P) after 3 hours.
Figure 17:
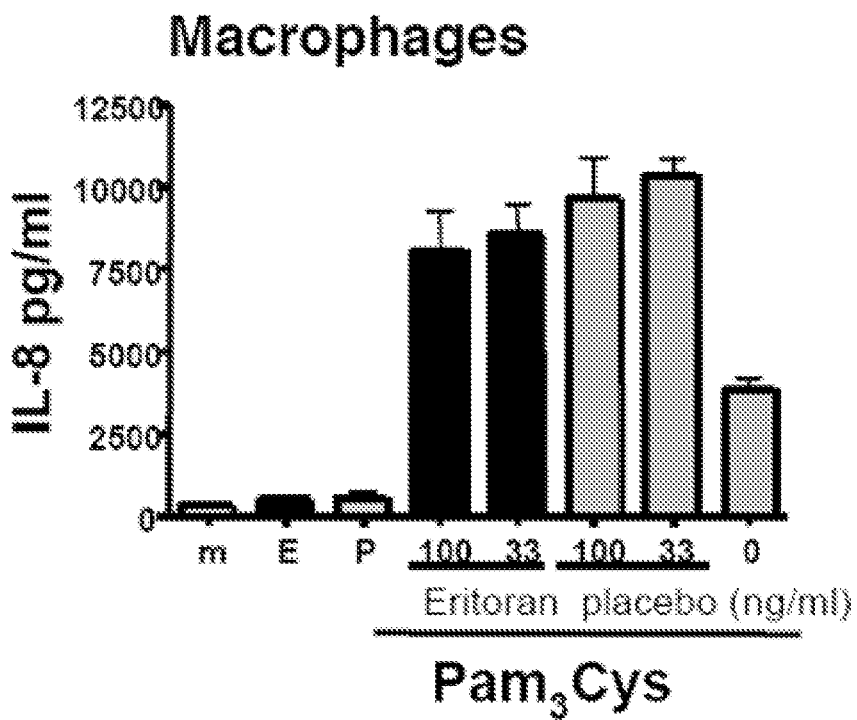
FIG. 17 illustrates a graph showing the IL-8 levels in the culture supernatant of macrophages (U937) stimulated with Pam3cys in the presence of eritoran tetrasodium (E) versus placebo (P) after 3 hours.
Figure 18:
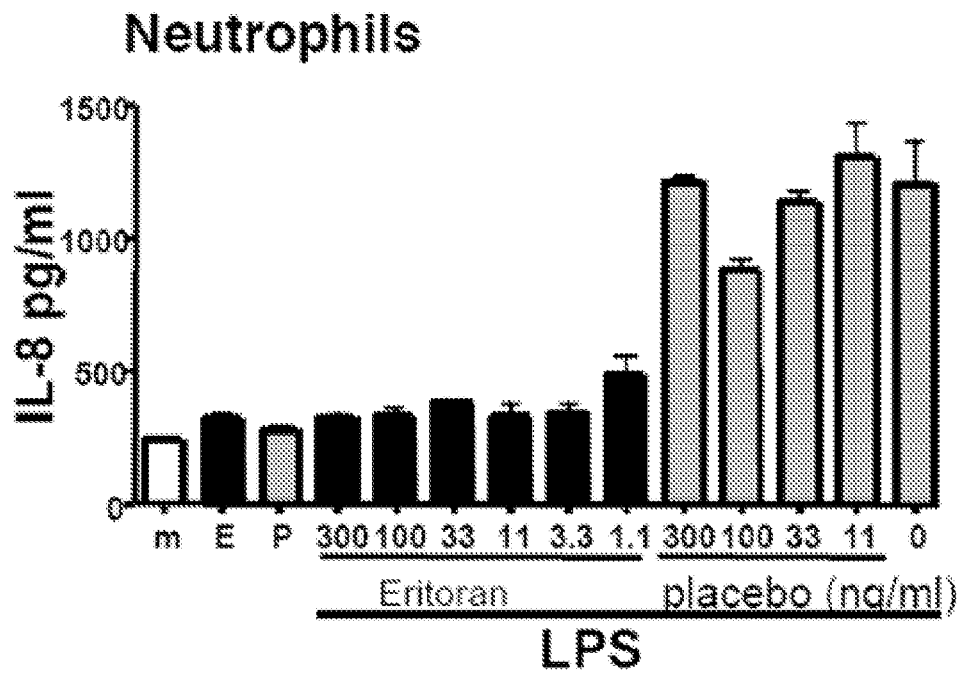
FIG. 18 illustrates a graph showing the IL-8 levels in the culture supernatant of neutrophils (HL60) stimulated with LPS in the presence of eritoran tetrasodium (E) versus placebo (P) after 3 hours.
Figure 19:
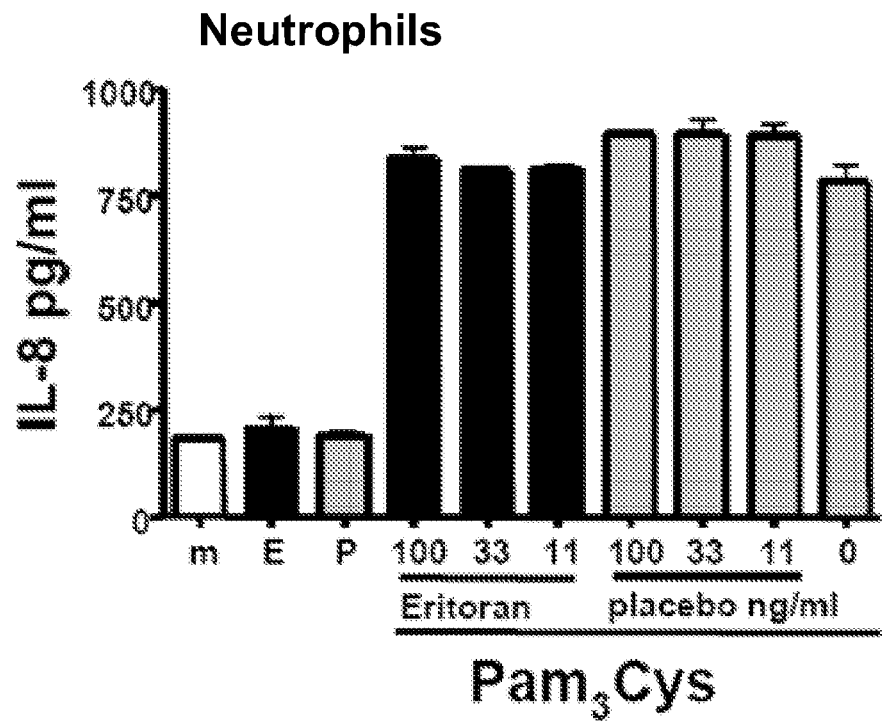
FIG. 19 illustrates a graph showing the IL-8 levels in the culture supernatant of neutrophils (HL60) stimulated with Pam3cys in the presence of eritoran tetrasodium (E) versus placebo (P) after 3 hours.

Cell lines derived from human corneal epithelial cells (HCE-T), macrophages (U937) and neutrophils (HL-60) were stimulated with LPS or Pam3Cys in the presence of eritoran tetrasodium or placebo. After 3 h (U937 and HL-60 cells) or 24 h (HCE-T cell), IL-8 levels in culture supernatants were quantified by ELISA. FIG. 14 shows HCE-T cells were incubated with 900 ng/ml LPS in the presence of 0.2 μg/ml exogenous MD-2 (essential for HCE responses to LPS) and indicated concentrations of Eritoran or placebo. Controls, which did not respond, include MD-2 alone (M), Placebo alone (P), Eritoran alone (E), LPS in the absence of MD-2 (L). FIG. 15 shows corneal epithelial cells incubated with 500 ng/ml Pam$_3$Cys under similar conditions. FIGS. 16 and 17 show macrophages stimulated with 10 ng/ml LPS or 500 ng/ml Pam$_3$Cys in the presence of Eritoran or placebo. FIGS. 18 and 19 show neutrophils stimulated with 1 ng/ml LPS or 500 ng/ml Pam$_3$Cys and Eritoran or placebo. LPS concentrations were based on preliminary data showing optimal IL-8 production. Note dose dependent inhibition by Eritoran for each cell type for LPS, but not Pam$_3$Cys-stimulated cells. Graphs are mean+/−SEM of three wells per sample. Experiments were repeated three times with similar results.

FIGS. 14-19 show each cell type produced IL-8 in response to LPS. Furthermore, eritoran tetrasodium inhibited LPS-induced IL-8 production in a dose dependent manner, whereas there was no effect on Pam3Cys-induced responses. The macrophage and neutrophil cell lines produced high levels of IL-8, which as inhibited by 1 ng/ml eritoran tetrasodium. In contrast, human corneal epithelial cells, which respond to LPS only in the presence of exogenous MD-2, produced less IL-8 and required higher doses of eritoran tetrasodium to inhibit.

Example 16

Figure 20:
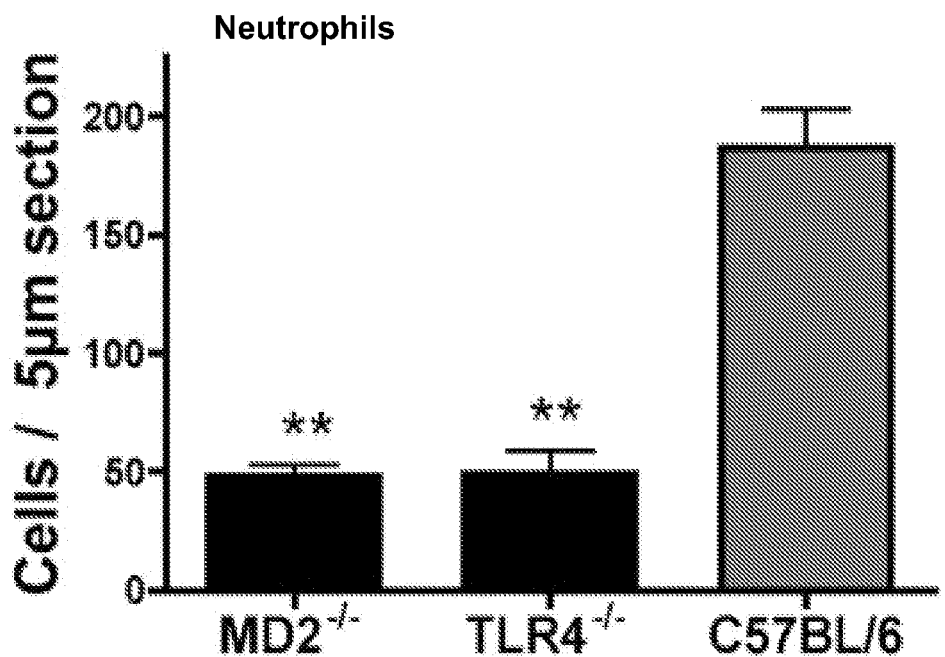
FIG. 20 illustrates a graph comparing neutrophil infiltrate in $P.$ $aeruginosa$-stimulated corneas of C57BL/6, TLR4$^{-/-}$ and MD-2$^{-/-}$ mice after 24 hours.
Figure 21:
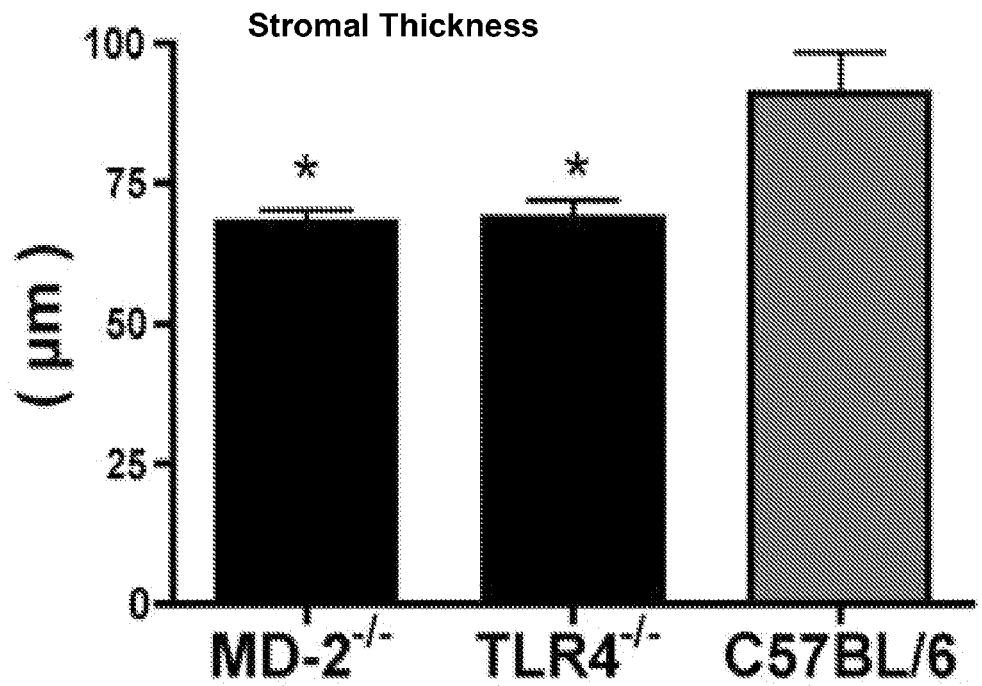
FIG. 21 illustrates a graph comparing stromal thickness in $P.$ $aeruginosa$-stimulated corneas of C57BL/6, TLR4$^{-/-}$ and MD-2$^{-/-}$ mice after 24 hours.
Figure 22:
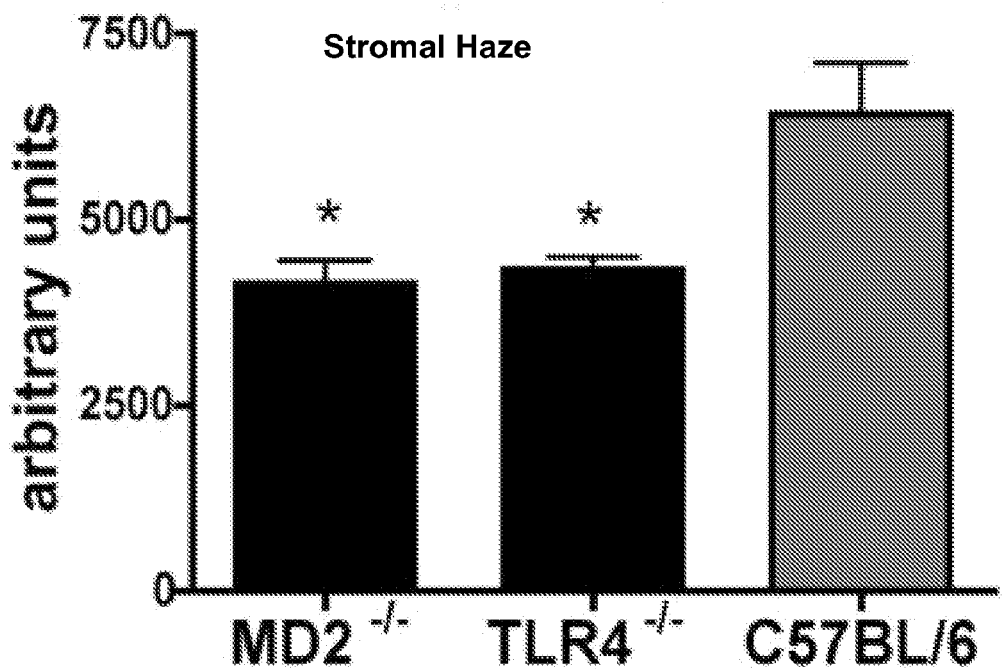
FIG. 22 illustrates a graph comparing stromal haze in $P.$ $aeruginosa$-stimulated corneas of C57BL/6, TLR4$^{-/-}$ and MD-2$^{-/-}$ mice after 24 hours.

Corneal Inflammation Induced by Antibiotic-Killed P. aeruginosa is TLR/4MD-2-Dependent and is Inhibited by Eritoran Tetrasodium As P. aeruginosa is a major cause of contact lens-related bacterial keratitis, we also examined the effect of eritoran tetrasodium in a model of P. aeruginosa-induced corneal inflammation. We found no difference in corneal inflammation induced by P. aeruginosa killed either by heat or after brief incubation with tobramycin (data not shown). To determine the role of TLR4 and MD-2 in P. aeruginosa-induced corneal inflammation, we incubated P. aeruginosa in tobramycin for 30 minutes to kill the bacteria (confirmed after plating) and added 2 μL bacterial suspension containing 1×10$^7$ organisms (in the presence of antibiotic) to the abraded corneal surface of C57BL/6, TLR4$^{-/-}$ and MD-2$^{-/-}$ mice. Bacteria were covered with a 2 mm diameter punch from a silicon hydrogel contact lens for 2 hours. After 24 hours, corneal inflammation was examined. FIGS. 20-22 shows P. aeruginosa-treated C57BL/6 corneas had a pronounced neutrophil infiltration to the corneal stroma; however, neutrophil infiltration, corneal thickness and corneal haze were significantly lower in TLR4$^{-/-}$ and MD-2$^{-/-}$ corneas compared with C57BL/6 corneas. Similar results were found for LPS (not shown).

Figure 23:
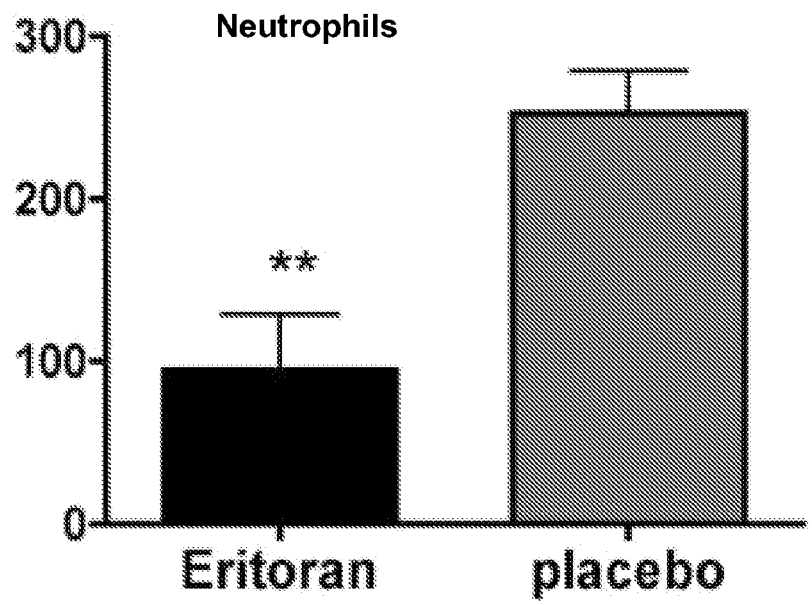
FIG. 23 illustrates a graph comparing neutrophil infiltrate in $P.$ $aeruginosa$-stimulated corneas of C57BL/6 mice treated with eritoran tetrasodium or placebo after 24 hours.
Figure 24:
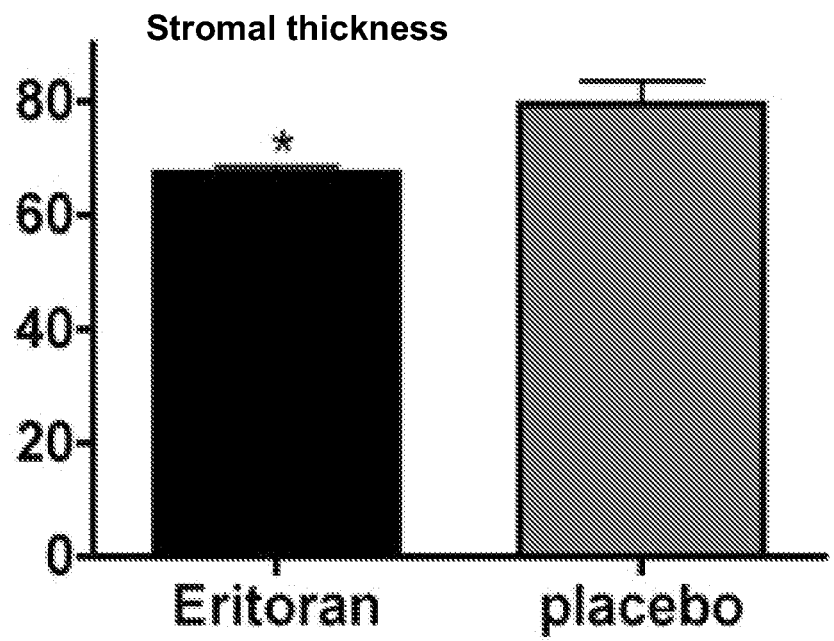
FIG. 24 illustrates a graph comparing stromal thickness in $P.$ $aeruginosa$-stimulated corneas of C57BL/6 mice treated with eritoran tetrasodium or placebo after 24 hours.
Figure 25:
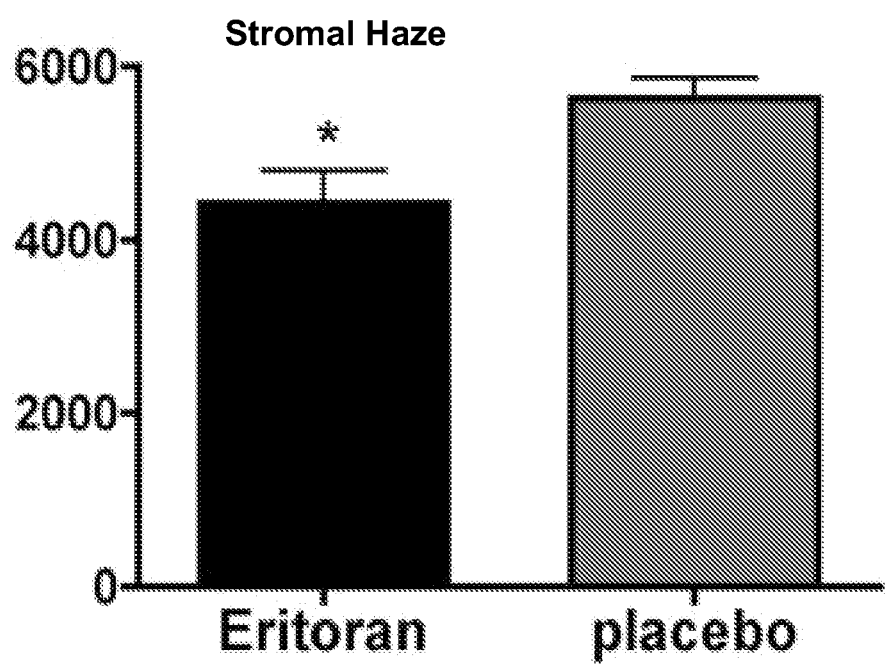
FIG. 25 illustrates a graph comparing stromal haze in $P.$ $aeruginosa$-stimulated corneas of C57BL/6 mice treated with eritoran tetrasodium or placebo after 24 hours.

FIGS. 23-25 show that when tobramycin-killed P. aeruginosa were added to corneas in the presence of eritoran tetrasodium (2.2 μg eritoran tetrasodium in 2 μL H$_2$O), each of these markers of corneal inflammation were significantly inhibited compared with placebo. These findings indicate that corneal inflammation induced by antibiotic-killed P. aeruginosa is TLR4/MD-2 dependent and can be inhibited by eritoran tetrasodium.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating corneal inflammation in a subject comprising
    topically administering to the subject a therapeutically effective amount of a TLR4 antagonist to treat corneal inflammation in the subject, wherein the TLR4 antagonist is a compound of formula (I):

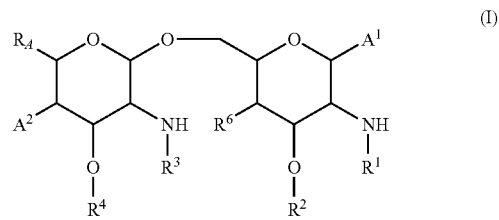

where R$^1$ is selected from the group consisting of:

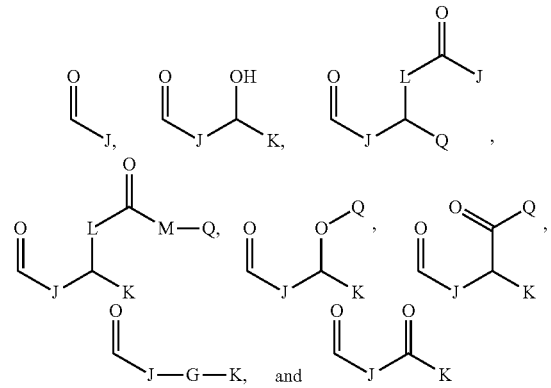

where each J, K, and Q, independently, is straight or branched C1 to C15 alkyl; L is O, NH, or CH$_2$; M is O or NH; and G is NH, O, S, SO, or SO$_2$;
R$^2$ is straight or branched C5 to C15 alkyl;
R$^3$ is selected from the group consisting of straight or branched C5 to C18 acyl,

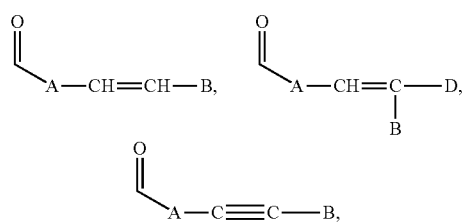

-continued

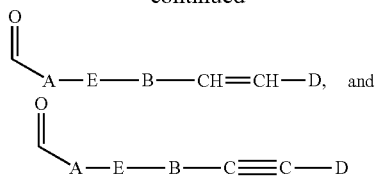

where E is NH, O, S, SO, or $SO_2$; each A, B, and D, independently, is straight or branched C1 to C15 alkyl;

$R^4$ is selected from the group consisting of straight or branched C4 to C20 alkyl, and

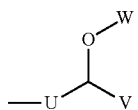

where each U and V, independently, is straight or branched C2 to C15 alkyl and W is hydrogen or straight or branched C1 to C5 alkyl;

$R_4$ is $R^5$ or $R^5$—O—$CH_2$—, $R^5$ being selected from the group consisting of hydrogen, J', -J'-OH, -J'-O—K', -J-O—K'—OH, and -J'-O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of OH,

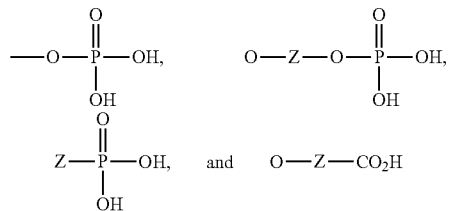

where Z is straight or branched C1 to C10 alkyl;
or pharmaceutically acceptable salt or phosphate ester thereof.

2. The method of claim 1, wherein the TLR4 antagonist is a compound of formula (II):

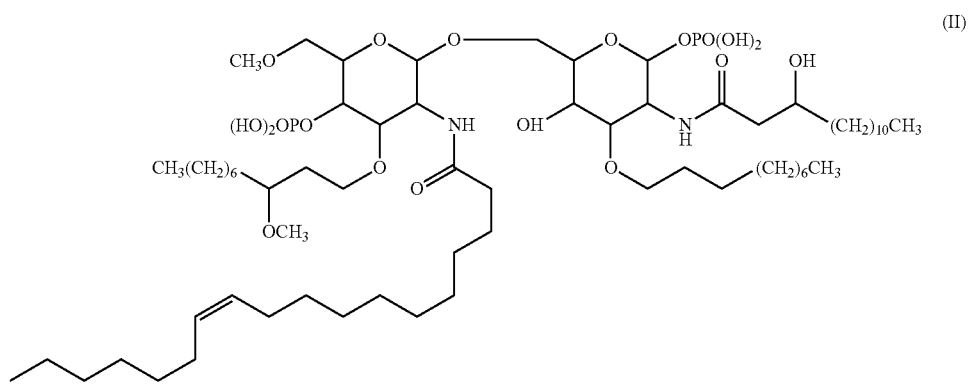

or a pharmaceutically acceptable salt or phosphate ester thereof.

3. The method of claim 2, wherein the TLR4 antagonist compound of formula (II) has the structure:

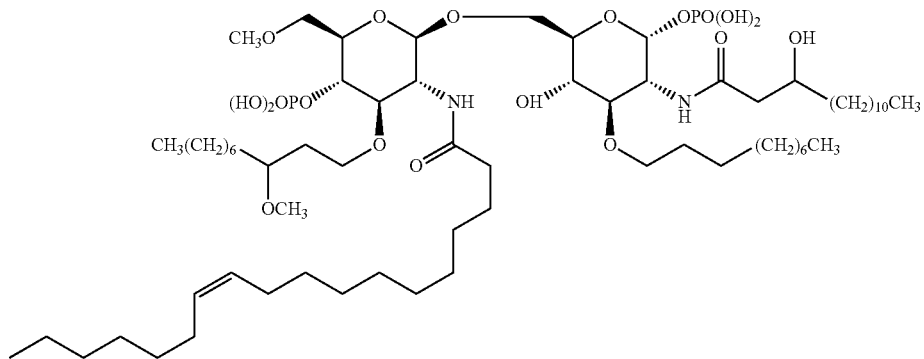

or a pharmaceutically acceptable salt or phosphate ester thereof.

4. The method of claim 2, wherein the TLR4 antagonist compound of formula (II) has the structure:

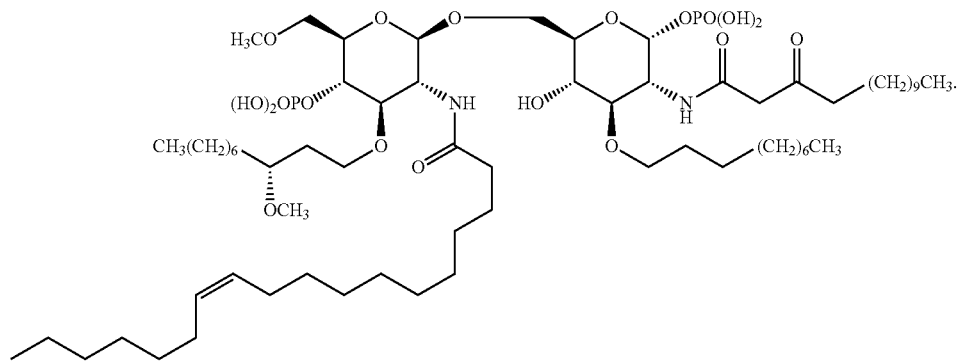

5. The method of claim 1, wherein the corneal inflammation is LPS induced corneal inflammation.

6. The method of claim 1, the subject not having corneal inflammation, but being at risk of developing corneal inflammation.

7. The method of claim 1, the subject having corneal inflammation.

8. The method of claim 1, the TLR4 antagonist being administered to the subject in an ophthalmic preparation.

9. The method of claim 1, the corneal inflammation being associated with keratitis.

10. The method of claim 1, the corneal inflammation being associated with sterile corneal inflammation.

11. The method of claim 1, the corneal inflammation being associated with contact lens wear.

12. A method of inhibiting corneal inflammation in a subject associated with contact lens wear comprising:

topically administering to the subject a therapeutically effective amount of a TLR4 antagonist to treat corneal inflammation associated with contact lens wear in the subject, wherein the TLR4 antagonist is a compound of formula (I):

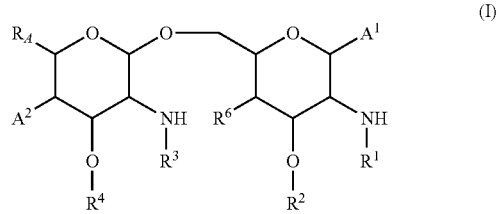

where $R^1$ is selected from the group consisting of:

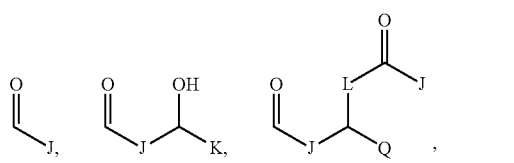

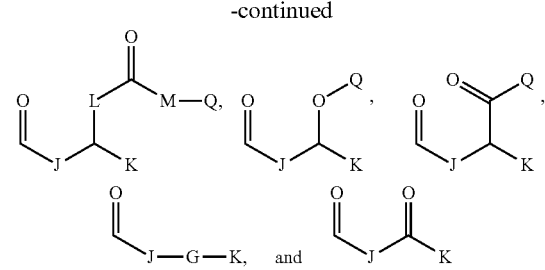

where each J, K, and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 acyl,

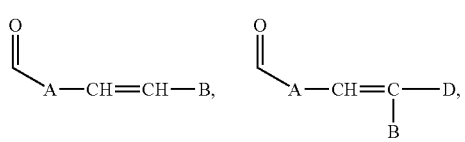

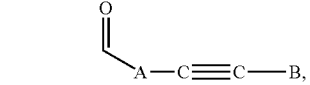

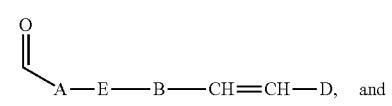

where E is NH, O, S, SO, or $SO_2$; each A, B, and D, independently, is straight or branched C1 to C15 alkyl;

$R^4$ is selected from the group consisting of straight or branched C4 to C20 alkyl, and

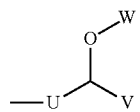

where each U and V, independently, is straight or branched C2 to C15 alkyl and W is hydrogen or straight or branched C1 to C5 alkyl;

$R_4$ is $R^5$ or $R^5$—O—$CH_2$—, $R^5$ being selected from the group consisting of hydrogen, J', -J'-OH, -J'-O—K', -J-O—K'—OH, and -J'-O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of OH,

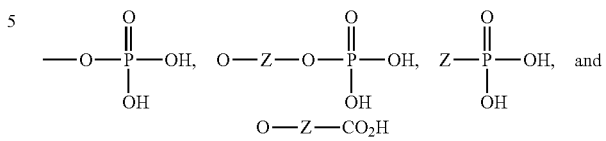

where Z is straight or branched C1 to C10 alkyl;

or pharmaceutically acceptable salt or phosphate ester thereof.

13. The method of claim 12, wherein the TLR4 antagonist is a compound of formula (II):

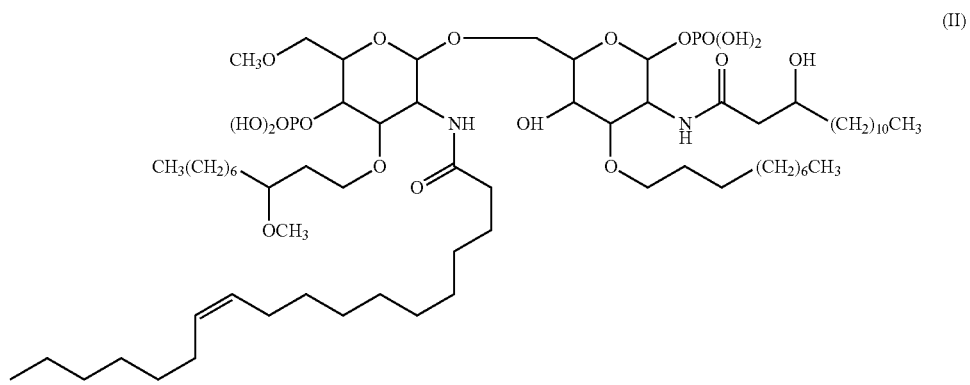

(II)

or a pharmaceutically acceptable salt or phosphate ester thereof.

14. The method of claim 13, wherein the TLR4 antagonist compound of formula (II) has the structure:

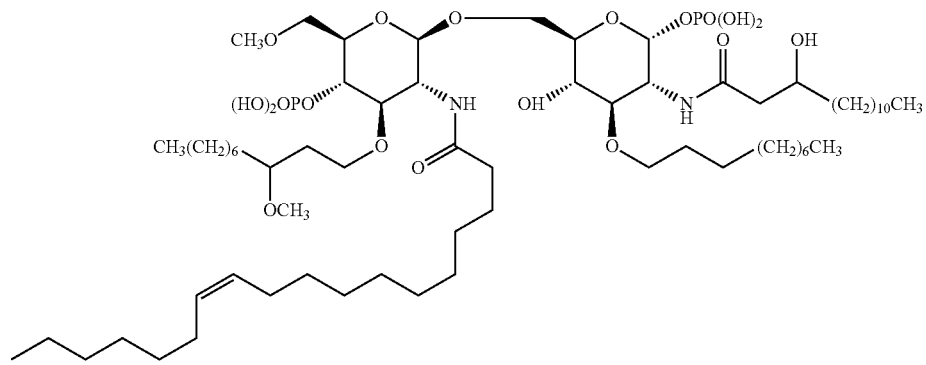

or a pharmaceutically acceptable salt or phosphate ester thereof.

15. The method of claim 13, wherein the TLR4 antagonist compound of formula (II) has the structure:

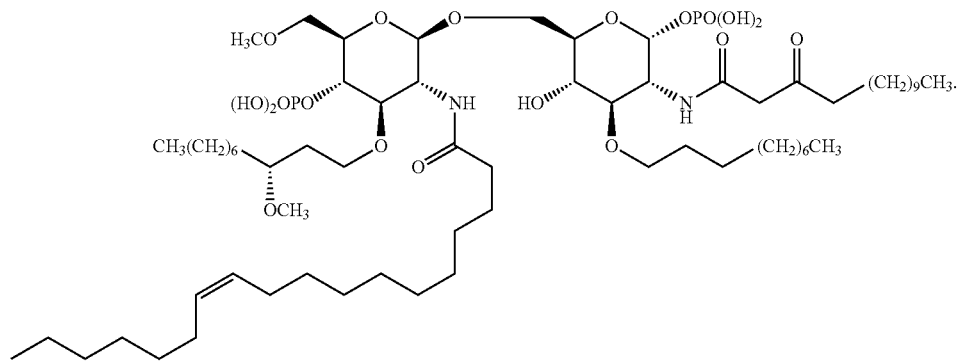

16. The method of claim 12, wherein the corneal inflammation is LPS induced corneal inflammation.

17. The method of claim 12, the subject not having corneal inflammation, but being at risk of developing corneal inflammation.

18. The method of claim 12, the subject having corneal inflammation.

19. The method of claim 12, the TLR4 antagonist being administered to the subject in an ophthalmic preparation.

20. A method of treating infectious keratitis in a subject comprising:
topically administering to the subject a therapeutically effective amount of a TLR4 antagonist to treat corneal inflammation in the subject and at least one antibacterial agent, antifungal agent, or antiviral agent, wherein the TLR4 antagonist is a compound of formula (I):

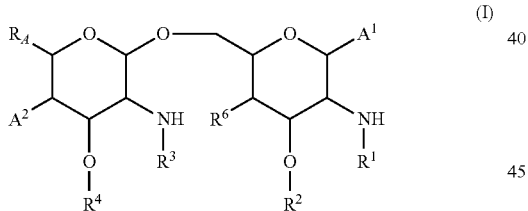

where $R^1$ is selected from the group consisting of:

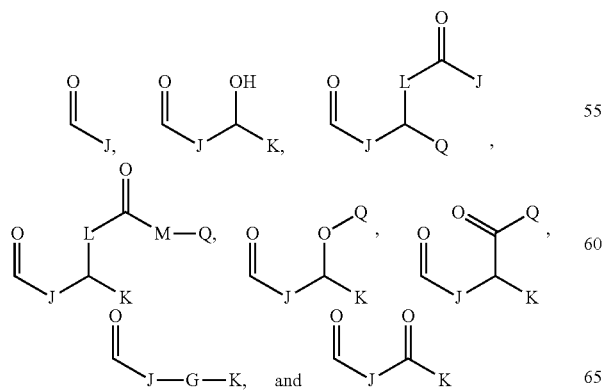

where each J, K, and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of straight or branched C5 to C18 acyl,

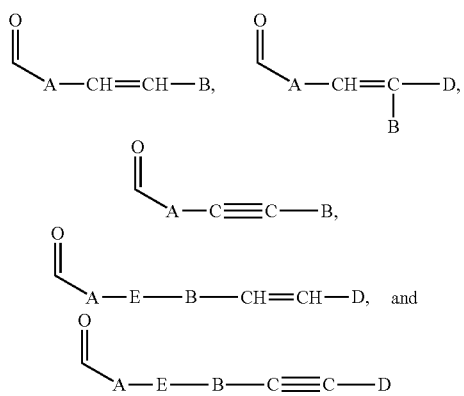

where E is NH, O, S, SO, or $SO_2$; each A, B, and D, independently, is straight or branched C1 to C15 alkyl;

$R^4$ is selected from the group consisting of straight or branched C4 to C20 alkyl, and

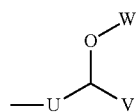

where each U and V, independently, is straight or branched C2 to C15 alkyl and W is hydrogen or straight or branched C1 to C5 alkyl;

$R_A$ is $R^5$ or $R^5$—O—$CH_2$—, $R^5$ being selected from the group consisting of hydrogen, J', -J'-OH, -J-O—K', -J'-O—K'—OH, and -J'-O—PO(OH)$_2$, where each J' and K', independently, is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of OH,

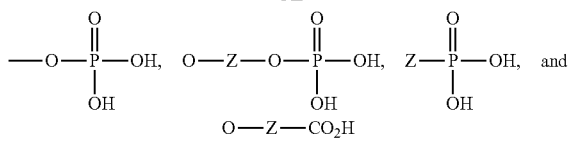

where Z is straight or branched C1 to C10 alkyl;

or pharmaceutically acceptable salt or phosphate ester thereof.

21. The method of claim 20, wherein the TLR4 antagonist is a compound of formula (II):

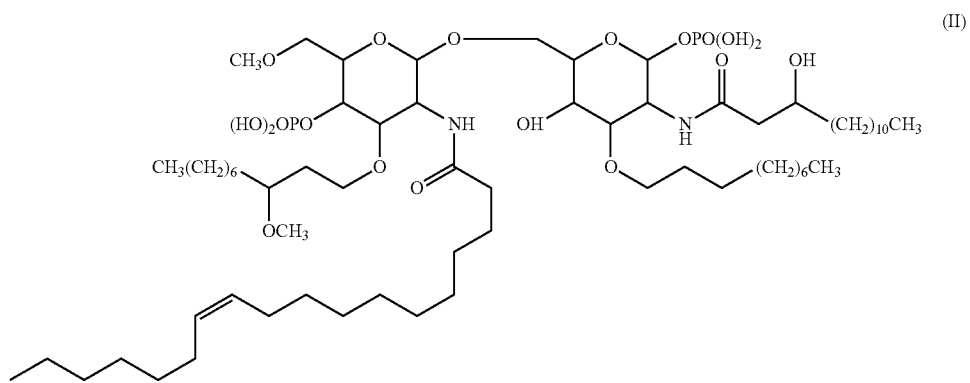

or a pharmaceutically acceptable salt or phosphate ester thereof.

22. The method of claim 21, wherein the TLR4 antagonist compound of formula (II) has the structure:

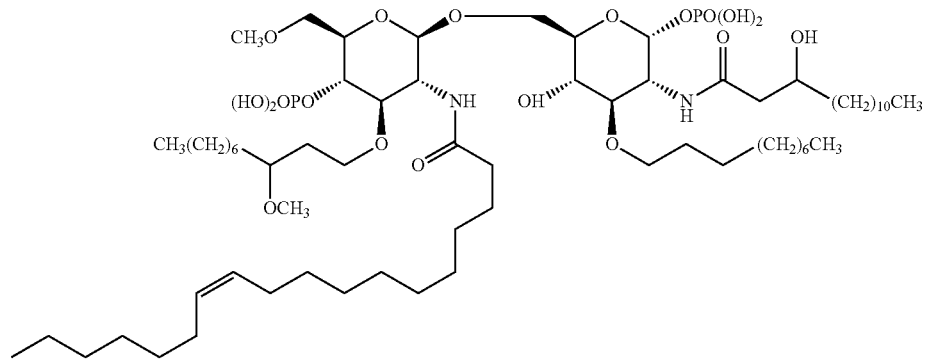

or a pharmaceutically acceptable salt or phosphate ester thereof.

23. The method of claim 21, wherein the TLR4 antagonist compound of formula (II) has the structure:

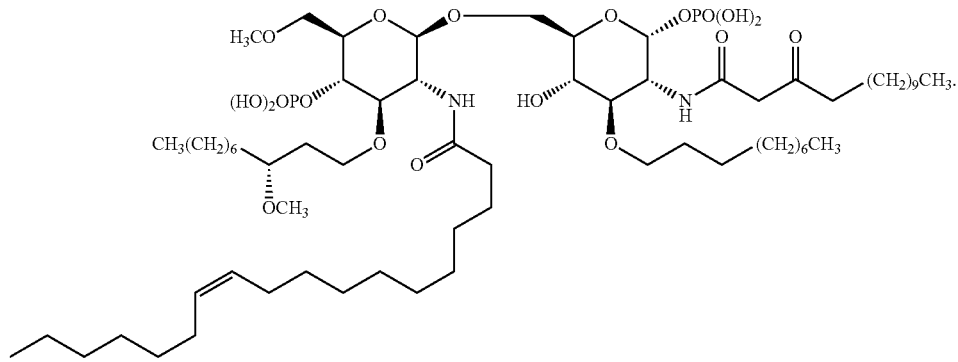

24. The method of claim 20, the TLR4 antagonist being administered to the subject in an ophthalmic preparation.

25. The method of claim 20, the at least one antibacterial agent, antifungal agent, or antiviral agent being administered in an ophthalmic preparation.

26. The method of claim 25, the infectious keratitis comprising bacterial keratitis and the ophthalmic preparation including an antibacterial agent.

* * * * *